(12) United States Patent
Kassab

(10) Patent No.: US 9,108,000 B2
(45) Date of Patent: *Aug. 18, 2015

(54) DEVICES, SYSTEMS, AND METHODS FOR AUTO-RETROPERFUSION OF THE CEREBRAL VENOUS SYSTEM

(71) Applicant: CVDevices, LLC, Zionsvlle, IN (US)

(72) Inventor: Ghassan S. Kassab, Zionsville, IN (US)

(73) Assignee: CVDevices, LLC, San Diego, CA (US)

( * ) Notice: Subject to any disclaimer, the term of this patent is extended or adjusted under 35 U.S.C. 154(b) by 291 days.

This patent is subject to a terminal disclaimer.

(21) Appl. No.: 13/705,101

(22) Filed: Dec. 4, 2012

(65) Prior Publication Data

US 2013/0096494 A1 Apr. 18, 2013

Related U.S. Application Data

(63) Continuation of application No. 12/715,100, filed on Mar. 1, 2010, now Pat. No. 8,322,347.

(51) Int. Cl.
*A61M 29/00* (2006.01)
*A61M 31/00* (2006.01)
(Continued)

(52) U.S. Cl.
CPC ............ *A61M 5/172* (2013.01); *A61B 5/02152* (2013.01); *A61B 5/02158* (2013.01);
(Continued)

(58) Field of Classification Search
CPC ........... A61B 5/02152; A61B 5/02158; A61B 5/026; A61B 5/145; A61B 5/6853; A61M 1/3621; A61M 2025/0002; A61M 2025/0681; A61M 2025/1081; A61M 2210/0693; A61M 25/007; A61M 25/1011; A61M 5/172; A61M 1/3613; A61M 2001/36

USPC ...................................................... 604/99.04
See application file for complete search history.

(56) References Cited

U.S. PATENT DOCUMENTS 4,459,977 A 7/1984 Pizon et al.
4,830,003 A 5/1989 Wolff et al.
(Continued)

OTHER PUBLICATIONS

Hirotani, Takashi, MD, Aortic Arch Repair Using the Hypothermic Circulatory Arrest Technique, 2001, 2nd Virtual Congress of Cardiology.

(Continued)

*Primary Examiner* — Jason Flick
(74) *Attorney, Agent, or Firm* — Reichel Stohry LLP; Mark C. Reichel; Natalie J. Dean

(57) ABSTRACT

Devices, systems, and methods for auto-retroperfusion of the cerebral venous system. In an exemplary embodiment of a catheter for controlling blood perfusion pressure of the present disclosure, the catheter comprises a body having a proximal open end, a distal end, a lumen extending between the proximal open end and the distal end, and a plurality of orifices disposed thereon, each of the orifices in fluid communication with the lumen, at least one expandable balloon, each of the at least one expandable balloons coupled with the body, having an interior that is in fluid communication with the lumen and adapted to move between an expanded configuration and a deflated configuration, and at least one sensor coupled with the distal end of the body, each of the at least one sensors adapted to gather data relating to a fluid flowing through the lumen, wherein the catheter is configured to be coupled to a flow unit for regulating the flow and pressure of a fluid.

20 Claims, 12 Drawing Sheets

(51) Int. Cl.
*A61M 5/172* (2006.01)
*A61B 5/0215* (2006.01)
*A61B 5/00* (2006.01)
*A61M 1/36* (2006.01)
*A61M 25/10* (2013.01)
*A61B 5/026* (2006.01)
*A61B 5/145* (2006.01)
*A61M 25/00* (2006.01)
*A61M 25/06* (2006.01)

(52) U.S. Cl.
CPC .......... *A61B5/6853* (2013.01); *A61M 1/3613* (2014.02); *A61M 1/3621* (2013.01); *A61M 25/1011* (2013.01); *A61B 5/026* (2013.01); *A61B 5/145* (2013.01); *A61M 25/007* (2013.01); *A61M 2025/0002* (2013.01); *A61M 2025/0681* (2013.01); *A61M 2025/1081* (2013.01); *A61M 2210/0693* (2013.01)

(56) References Cited

U.S. PATENT DOCUMENTS

| | | |
|---|---|---|
| 5,295,969 A | 3/1994 | Fischell et al. |
| 5,597,377 A | 1/1997 | Aldea |
| 5,700,447 A | 12/1997 | Bucala et al. |
| 5,794,629 A | 8/1998 | Frazee |
| 5,908,407 A | 6/1999 | Frazee et al. |
| 5,919,163 A | 7/1999 | Glickman |
| 6,083,198 A | 7/2000 | Afzal |
| 6,299,619 B1 | 10/2001 | Greene et al. |
| 6,312,421 B1 | 11/2001 | Boock |
| 6,461,327 B1 | 10/2002 | Addis et al. |
| 6,500,145 B1 | 12/2002 | Bicakci et al. |
| 6,508,777 B1 | 1/2003 | Macoviak et al. |
| 6,792,302 B2 | 9/2004 | Wintermark et al. |
| 6,855,291 B2 | 2/2005 | Patterson et al. |
| 7,004,926 B2 | 2/2006 | Navia et al. |
| 2002/0077581 A1 | 6/2002 | Davidner et al. |
| 2002/0161321 A1* | 10/2002 | Sweezer et al. ............ 604/6.14 |
| 2004/0044351 A1 | 3/2004 | Searle |
| 2006/0047262 A1* | 3/2006 | Barbut et al. ............. 604/509 |
| 2010/0204634 A1 | 8/2010 | Baxter et al. |

OTHER PUBLICATIONS

Esmailian et al., Retrograde Cerebral Perfusion as an Adjunct to Prolonged Hypothermic Circulatory Arrest, Chest, 1999, 116(4): 887-891, American College of Chest Physicians, Northbrook, Illinois, USA.

* cited by examiner

DEVICES, SYSTEMS, AND METHODS FOR AUTO-RETROPERFUSION OF THE CEREBRAL VENOUS SYSTEM

PRIORITY

The present application is related to, claims the priority benefit of, and is a continuation application of, U.S. Nonprovisional application Ser. No. 12/715,100, filed Mar. 1, 2010 and issued as U.S. Pat. No. 8,322,347 on Dec. 4, 2012, which is related to, claims the priority benefit of, and is a continuation application of, U.S. Nonprovisional patent application Ser. No. 12/715,046, filed Mar. 1, 2010 and issued as U.S. Pat. No. 8,241,248 on Aug. 14, 2012, which is related to, and claims the priority benefit of, U.S. Provisional Patent Application No. 61/156,458, filed on Feb. 27, 2009. The contents of each of these applications are hereby incorporated by reference in their entirety into this disclosure.

BACKGROUND

Globally, stroke has a major impact on public health as it is the second most common cause of death and a major cause of disability. It is estimated that around 700,000 people experience a transient ischemic attack or stroke annually in the United States alone. Of those 700,000 people, it is estimated about 200,000 experience a recurrent stroke at a later date. As such, stroke survivors as a group have an increased risk of experiencing an additional stroke(s) and, unsurprisingly, have increased mortality and morbidity rates.

National projections for the period between 2006 and 2025 predict around 1.5 million new cases of ischemic stroke in men and 1.9 million new cases in women. The total projected cost of stroke and the resultant disability associated therewith is estimated to be around $2.2 trillion in the United States alone, including direct and indirect costs such as ambulance services, initial hospitalization, rehabilitation, nursing home costs, outpatient visits, drugs, informal care-giving, and lost potential earnings. Accordingly, the cost of this illness to society in both health care and lost productivity is enormous, and the extended complications associated with surviving even one stroke event adversely influences both quality of life, and the morbidity and mortality of the individual stroke survivor.

Viability of the cerebral tissue depends on cerebral blood flow. During a stroke, a portion of brain tissue known as the ischemic lesion is deprived of sufficient blood flow due to an arterial occlusion (i.e. a blood clot). Within the ischemic cerebrovascular bed caused by an acute ischemic stroke, there are two major zones of injury: the core ischemic zone and the ischemic penumbra. In the core zone, which is an area of severe ischemia (blood flow reduced to below 15-20 ml/100 g/minute), the loss of an adequate supply of oxygen and glucose results in the rapid depletion of energy stores resulting in death of the brain tissue. As neurons die within a few minutes of oxygen deprivation, neuronal death begins to occur in areas of no blood flow within minutes of stroke onset, thus leaving the tissue of the core ischemic zone unable to function.

Surrounding such areas of necrosis is a transitional region of hypoperfused, electronically silent tissue that barely receives enough blood flow to keep the neurons alive. Brain cells within this transitional region, the penumbra, are functionally compromised, but not yet irreversibly damaged. Accordingly, the ischemic penumbra may remain viable for several hours after ischemic onset and therefore is the major focus of most therapeutic procedures for resuscitation of acute stroke patients.

When the systemic pressure of the brain lowers, cerebral perfusion autoregulation reflexes allow for vasodilation in order to keep a constant cerebral blood flow. This vascular dilation leads in turn to an increased cerebral blood volume, at least within the salvageable penumbra. (Contrary to the penumbral regions, the autoregulation processes are compromised in the area of the core ischemic infarct itself and therefore both CBV and cerebral blood flow are diminished thereto.) In the penumbra, cerebral perfusion autoregulation reflexes automatically adjust the regional cerebral blood volume and ensure cerebral blood flow stability despite changes in systemic arterial pressure caused by the underlying arterial occlusion. In this manner, the regional cerebral blood volume may be greater than 2.5 milliliters per 100 g in the penumbral area.

Through mapping the cerebral blood volume and the cerebral blood flow, it is possible to locate the penumbra-infarct area regions of the brain, with diminution in both cerebral blood flow and cerebral blood volume corresponding to the core ischemic zone and regions with a decreased cerebral blood flow, yet increased of cerebral blood volume corresponding to the penumbra. Recognition of the penumbra through modern neuroimaging techniques (e.g., computed tomography and magnetic resonance imaging) may be used to identify patients who are more likely to benefit from therapeutic intervention.

Typically, a window of viability exists during which the neurons within the ischemic penumbra may recover if the area is reperfused. This window of viability exists because the penumbral region is supplied with blood through collateral arteries anastomosing with branches of the occluded vascular tree and is subjected to increased cerebral blood volume as previously discussed. However, if reperfusion is not established relatively quickly following the acute attack, over time irretrievable infarction will progressively replace the cells in the penumbral region. This replacement rate varies according to the collateral circulation levels and is often patient and event specific. On average, a clinician typically has between about two (2) to three (3) hours following the onset of an acute ischemic stroke event during which to reperfuse the ischemic penumbral region; however, this timeframe may be shorter or extend as long as twenty-two (22) hours from acute onset, depending on the particular patient and other factors. Because the penumbra has the potential for recovery and survival of the neurons in the penumbral region is associated with better prognostics, the penumbra is an important therapeutic target to be considered for interventional therapy in acute ischemic stroke patients.

Despite advances in the understanding of stroke pathogenesis, until recently, no specific therapeutic procedures have been available for improving outcomes in acute stroke patients. However, due to recent therapeutic developments, the morbidity and mortality of acute stroke patients has seen an overall decline. For example, the availability of general acute management in a stroke unit, medication through aspirin within forty-eight (48) hours of acute onset, and the intravenous use of thrombolytic therapies within three (3) hours of acute onset have contributed to the reduction seen in the morbidity and mortality of acute stoke patients. While these therapies have shown favorable results, all of these therapeutic procedures require that the patient is treated immediately after or within a short time of stroke onset in order to prevent or minimize neuron death. Accordingly, a need exists to extend the window of time during which the penumbra is viable, and thus the time during which the thrombolytic therapy may be effective, in order to further improve efficacy of the procedures and reduce associated complication rates.

There is currently little understanding of how to use prophylactic therapies in patients suffering from an acute ischemic stroke. For example, the rigid time window where the penumbral region remains viable greatly limits the availability of thrombolytic treatment in the majority of cases. Further, for more than two (2) decades, neurologists have sought a drug that protects ischemic brain tissue from cell death with little success; the list of pharmaceuticals tested in Phase II and Phase III trials is extensive, yet none have proved effective in humans. Other neuroprotective agents such as radical scavengers, calcium antagonists, sodium or potassium channel blockers, cell membrane stabilizers, anti-inflammatory agents, anti-adhesion molecules, and glycine-, AMPA- and serotonin-receptor antagonists have proven to significantly reduce the infarct volume in animal models, yet also were found ineffective in clinical trials. One reason such pharmaceutical and/or thrombolytic therapies have been found ineffective in humans is that it is unlikely that the drugs, especially neuroprotective agents, can reach high enough pharmacological levels in the penumbral region to prevent the progression of tissue damage therein prior to the onset of cellular death. Accordingly, the combination of neuroprotective drug therapies and thrombolytic treatments in particular may be mandatory to overcome these hurdles within the short three (3) hour window where the cells remain viable.

One technique that has not conventionally been applied in the treatment of stroke victims is retrograde cerebral perfusion ("RCP") therapies. RCP has been applied for more than a decade in connection with aortic arch surgeries requiring hypothermic circulatory arrest. One of the first uses of RCP was reported in 1994, for periods lasting between twenty-seven (27) and eighty-one (81) minutes. All of the patients who were the subjects of that study returned to consciousness within four (4) hours of the procedure and there was no record of detectable neurologic defects that arose postoperatively. As previously noted, since these initial trials, RCP has been used extensively in connection with similar procedures. Recent clinical reports suggest that circulation management using RCP in combination with hypothermic circulatory arrest has even decreased the overall rate of stroke and operative mortality associated with aortic arch operations.

The advantages of RCP for use in connection with aortic arch surgeries have been well delineated, such as continuous delivery of metabolic substrates to the brain (e.g., oxygen and other cellular nutrients), removal of toxic metabolites and possible embolism (i.e. air or particulates), and better preservation of uniform hypothermia. Further, other theoretical advantages of RCP have been suggested, such as flushing of gaseous or atheromatous debris and the ease of establishment without the need for any additional cannulas.

Although RCP has been very successful for patients undergoing circulatory arrest in surgery, a bridge reperfusion therapy used in conjunction with thrombolytics and/or other pharmaceuticals for stroke patients does not currently exist. Accordingly, a need exists for a device, system and method for providing stroke patients with sufficient blood flow to the penumbra in order to nourish the brain tissue such that thrombolytic or other pharmaceutical agents are provided with a sufficient amount of time in which they can establish the necessary pharmacological concentrations in the area of interest and effectively perform the intended pharmacological function.

BRIEF SUMMARY

Devices and systems are described for providing retroperfusion and autoretroperfusion therapies to a brain. In certain embodiments, a catheter for controlling blood perfusion pressure is provided. The catheter comprises a body, at least one expandable balloon and at least one sensor coupled with the body. The body of the catheter comprises a proximal open end, a distal end, a lumen extending between the proximal open end and the distal end, and a plurality of orifices disposed thereon. Each of the orifices is in fluid communication with the lumen of the catheter body. In at least one embodiment, the body of the catheter is configured for placement within a venous vessel. Further, the lumen of the body may optionally be configured to slidably receive at least one guidewire therethrough, and the distal end of the body may be configured to allow the at least one guidewire to extend therethrough.

Each of the at least one expandable balloons of the catheter is coupled with the body and comprises an interior that is in fluid communication with the lumen. Further, each expandable balloon is adapted to move between an expanded configuration and a deflated configuration. The body of the catheter may further comprise one or more pores disposed thereon to facilitate fluid communication between the lumen and the interior of teach of the at least one expandable balloons. In this embodiment, each of the at least one expandable balloons may be adapted to move from the deflated configuration to the expanded configuration when a fluid flows through the lumen of the body, through the one or more pores, and into the interior of the expandable balloon.

Each of the at least one sensors of the catheter is coupled with the distal end of the body and adapted to gather data relating to a fluid flowing through the lumen. Further, in at least one embodiment, the at least one sensor is adapted to transmit the gathered data to a remote device. The transmission of gathered data to the remote device may be achieved in various different manners. In at least one embodiment, at least one of the at least one sensors is coupled with a sensor capable. The sensor capable may be disposed within the interior of the lumen of the catheter such that the sensor cable extends through the proximal end of the body and is adapted to transmit the gathered data to the remote device.

The catheter described herein may further comprise a sheath. The sheath comprises a proximal end, a distal end, and an interior. In at least one embodiment, the interior of the sheath is configured to slidably receive the body of the catheter therein.

A flow unit for regulating the flow and pressure of a fluid is also described herein. The flow unit comprises an elongated body having an open proximal end, an open distal end, an interior extending between the open proximal end and the open distal end. The flow unit further comprises a chamber surrounding at least a portion of the elongated body. The chamber comprises an interior and at least one port in fluid communication with the interior of the chamber which is adapted to couple with a fluid source. The chamber of the flow unit is adapted to expand and deflate. In at least one embodiment, the section of the interior of the elongated body associated with the portion surrounded by the chamber comprises a first diameter when the chamber is deflated and a second diameter when the chamber is expanded. Here, the second diameter is less than the first diameter, such that the chamber reduces the size of the interior of the elongated body when the chamber is expanded. Further, the interior of the chamber may be adapted to exert a compressive force on the portion of the elongated body surrounded thereby.

The flow unit further comprises at least one sensor disposed at or near the distal end of the elongated body of the flow unit. Each of the at least one sensors is adapted to gather data relating to the fluid flowing through the interior of the elongated body. In at least one embodiment of the flow unit, one or more of the at least one sensors is adapted to transmit the gathered data to a remote device. For example, and without limitation, the at least one sensor may be electronically coupled via a wire with the remote device.

In certain embodiments, the remote device may comprise a computer or any other processor known in the art. The remote device may be in communication with the fluid source coupled with the interior of the chamber via the at least one port. In at least one embodiment, the fluid source is adapted to inject or withdraw fluid—which may be a liquid or a gas—from the interior of the chamber in response to the gathered data received from the at least one sensor of the flow unit.

Systems for providing a retroperfusion therapy to a venous vessel comprising the above-described components are also provided herein. Specifically, a system for providing a retroperfusion therapy to a venous vessel comprises the catheter for controlling blood perfusion pressure and the flow unit for regulating the flow and pressure of a fluid, both of which are described above. In operation, the open distal end of the flow unit is coupled with the open proximal end of the body of the catheter such that fluid communication is established between the lumen of the catheter and the interior of the elongated body of the flow unit.

The system may further comprise a source of arterial blood flow comprising a proximal end, a distal end and an interior extending between the proximal end and the distal end. The distal end of the source of arterial blood flow is configured to couple with the proximal end of the elongated body of the flow unit. Each of the proximal end, the distal end and the interior of the source of arterial blood flow is configured to allow arterial blood to flow therethrough.

The remote device of the system may be in communication with the fluid source coupled with the flow unit. Further, the remote device may be adapted to receive the gathered data from the at least one sensor of the flow unit and process the gathered data to ascertain if the gathered data falls within one or more parameters. For example, in at least one embodiment, the one or more parameters may comprise flow rate of a fluid flowing through the interior of the elongated body of the flow unit, pressure of the fluid flowing through the interior of the elongated body of the flow unit, and/or perfusion rate of the fluid into the venous vessel. In at least one embodiment, the remote device is also adapted to automatically affect the flow of fluid to or from the fluid source when the gathered data falls outside of the one or more parameters.

The system may further comprise a connection assembly for providing a sterile environment. In at least one embodiment, the connection assembly comprises a cover, at least one valve in fluid communication with the cover, and at least one flushing port in fluid communication with the gas supply and the cover. The cover of the connection assembly comprises a body portion, a limb component extending from the body portion, and an interior extending between the body portion and the limb component. In at least one embodiment, the cover is corrugated. The interior of the cover configured to encase the distal end of the elongated body of the flow unit and the proximal end of the body of the catheter therein and further is in fluid communication with the at least one flushing port and the at least one valve of the connection assembly. Furthermore, the interior of the cover may be adapted to slidably receive at least one guidewire therethrough.

The at least one valve of the connection assembly is adapted to drain gas from within the interior of the cover. The at least one valve may optionally be adapted to automatically drain gas from within the interior of the cover when the pressure within the interior of the cover is greater than a set value. Furthermore, in at least one embodiment, the at least one valve comprises a one-way valve.

Kits comprising the above-described system are also disclosed herein. For example, in at least one embodiment, a kit comprising the following is described: a catheter for controlling blood perfusion pressure, the catheter comprising a body having a proximal open end, a distal end, a lumen extending between the proximal open end and the distal end, and a plurality of orifices disposed thereon, each of the orifices in fluid communication with the lumen, and at least one expandable balloon, each of the at least one expandable balloons coupled with the body, having an interior that is in fluid communication with the lumen and adapted to move between an expanded configuration and a deflated configuration; and a flow unit for regulating the flow and pressure of a fluid, the flow unit comprising an elongated body having an open proximal end, an open distal end, an interior extending between the open proximal end and the open distal end, and a chamber surrounding at least a portion of the elongated body, the chamber adapted to expand and deflate and comprising an interior and at least one port, the at least one port in fluid communication with the interior of the chamber and adapted to couple with a fluid source, and at least one sensor coupled with the distal end of the elongated body, each of the at least one sensors adapted to gather data and transmit the gathered data to a remote device. The kit may additionally comprise at least one guidewire and/or the connection assembly described herein for providing a sterile environment.

Methods for delivering a retroperfusion therapy to an ischemic area of a brain are also provided herein. In at least one embodiment, such a method comprises the steps of: identifying the location of a penumbral region within a brain; re-routing arterial blood flow from an artery into the proximal end of a first catheter for receiving arterial blood flow, the first catheter comprising a proximal end for receiving the arterial blood flow, a distal end for allowing the arterial blood flow to flow therethrough and an interior extending between the proximal end and the distal end; inserting a first guidewire into a vein and advancing the guidewire through the vein into the penumbral region of the brain; advancing a second catheter over the first guidewire, through the vein and into the penumbral region of the brain, the second catheter comprising an open proximal end, a distal end, an interior extending between the open proximal end and the distal end, and a plurality of orifices disposed thereon, each of the orifices in fluid communication with the interior of the second catheter; coupling the proximal end of the second catheter with a flow unit, the flow unit comprising an elongated body having an open proximal end configured to couple with the distal end of the first catheter, an open distal end configured to couple with the open proximal end of the second catheter, an interior extending between the open proximal end and the open distal end and configured to allow arterial blood to flow therethrough, and a chamber coupled with the elongated body and configured to regulate the flow rate and pressure of the arterial blood flow flowing through the interior of the flow unit; coupling the distal end of the first catheter with the proximal end of the flow unit such that the interior of the first catheter and the interior of the flow unit are in fluid communication; supplying the penumbral region of the brain with arterial blood flow by allowing the arterial blood to flow in a pulsatile fashion through the first catheter, into and through the interior of the flow unit, into and through the second catheter, and into the vein at the location within the penumbral region; and regulating the pressure and flow rate of the arterial blood flowing through the interior of the elongated body of the flow unit through operation of the chamber.

In certain embodiments of the method, the interior of the flow unit may comprise a diameter. In this embodiment, the step of regulating the pressure and flow rate of the arterial blood flowing through the interior of the elongated body of the flow unit through operation of the chamber may additionally comprise adjusting the diameter of the interior of the elongated body of the flow unit to affect the pressure and/or flow rate of the arterial blood flowing therethrough.

Further, in at least one embodiment of the method, the flow unit further comprises at least one sensor disposed at or near the open distal end of the elongated body and the first catheter further comprises at least one sensor disposed at or near the distal end thereof. Here, each of the at least one sensors is adapted to gather data and transmit the gathered data to a remote device. In this at least one embodiment, the method may further comprise the step of using the remote device to monitor the data gathered by the at least one sensor of the flow unit and the at least one sensor of the first catheter. Additionally, at least one embodiment of the method further comprises the step of processing the gathered data from the flow unit and the second catheter to ascertain if the gathered data falls within one or more programmed parameters.

The second catheter of the method may further comprise at least one expandable balloon, each of the at least one expandable balloons coupled with the first catheter, having an interior in fluid communication with the interior of the second catheter through one or more pores and adapted to move between an expanded configuration and a deflated configuration. In this at least one embodiment, wherein when the at least one balloon of the second catheter is in the expanded configuration, the at least one balloon of the second catheter occludes the vein and prevents antegrade flow of the arterial blood therethrough. Additionally, at least one embodiment of the method described herein further comprises the step of moving the at least one balloon of the second catheter from the deflated configuration to the expanded configuration in accordance with the pulsatile flow of the arterial blood through the interior of the second catheter.

In certain embodiments, the step of regulating the pressure and flow rate of the arterial blood flowing through the interior of the elongated body of the flow unit through operation of the chamber is automatically initiated by the remote device when the gathered data falls outside of the one or more programmed parameters. Further, the interior of the elongated body of the flow unit may comprise a diameter and the chamber of the flow unit surrounding at least a portion of the elongated body of the flow unit may comprises an interior defining a volume, and may be adapted to expand when the volume is increased and deflate when the volume is decreased; and the step of regulating the pressure and flow rate of the arterial blood flowing through the interior of the elongated body of the flow unit through operation of the chamber further may comprise adjusting the volume of the interior of the chamber such that the chamber compresses a section of the interior of the elongated body associated with the portion surrounded by the chamber thereby reducing the diameter of the interior of the elongated body.

The methods described herein may further comprise the step of defining an inherent pressure and flow cycle of the arterial blood flowing through the flow unit and establishing a sequence of injecting and withdrawing fluid from the interior of the chamber of the flow unit. Alternatively or additionally, the methods may further comprise the step of delivering a pharmaceutical agent to the brain.

In at least one embodiment of the method, the step of coupling the proximal end of the second catheter with a flow unit may be performed in a sterile environment provided by the connection assembly previously described herein. Here, the step of the method comprising coupling the proximal end of the second catheter with a flow unit may be performed in a sterile environment provided by a connection assembly comprises flushing the interior of the cover with a sterile gas. Furthermore, in at least one embodiment, the at least one valve of the connection assembly is adapted to automatically drain gas from within the interior of the cover when pressure within the interior of the cover is greater than a set value and the method further comprises the step of maintaining the pressure within the interior of the cover through operation of at least one of the at least one valves. Further, in the at least one embodiment of the connection assembly where the interior of the cover is configured to receive one or more guidewires therethrough, the method may further comprise the steps of inserting a second guidewire into a vein; advancing the second guidewire through the vein into a location proximate to the flow unit and the open proximal end of the second catheter; and advancing the connection assembly over the second guidewire, through the vein and to the location.

In those embodiments of the system further comprising the sheath, the method may further comprise the step of sliding the sheath over the second catheter such that one or more of the plurality of orifices are blocked and arterial blood flow is prevented from flowing through the blocked orifice(s).

DETAILED DESCRIPTION

Figure 1:
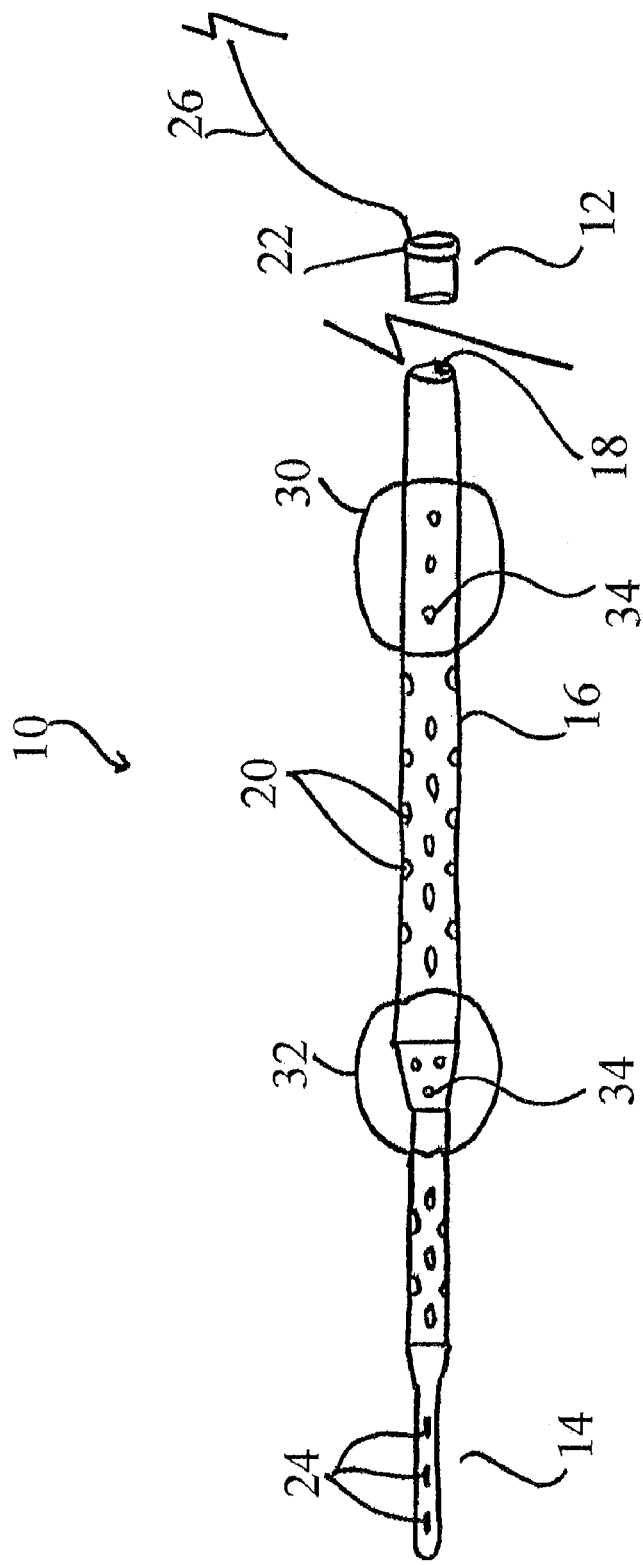
FIG. 1 shows a side view of one embodiment of a catheter for delivering arterial blood within a venous vessel.

Reference will now be made to the embodiments illustrated in the drawings and specific language will be used to describe the same. It will nevertheless be understood that no limitation of scope is intended by the description of these embodiments.

The devices, systems and methods described herein provide for a bridge therapy that is capable of supplying a patient's own oxygenated arterial blood to the compromised penumbral region of the brain via cerebral pulsatile venous retroperfusion. In this manner, the devices, systems and methods described herein facilitate the provision of oxygen-rich blood to the penumbra and thereby extend the window during which the penumbral cells remain viable. Extending the window of viability of the penumbra allows for the use of several new therapies for the treatment of stroke including, without limitation, the delivery of neuroprotective agents and thrombolytic drugs to the cerebral venous system as the agents and drugs will be allowed a sufficient period of time to become pharmaceutically effective.

The normal human brain weighs about 1,500 grams and contains about 75 milliliters of blood. Of the 75 milliliters of blood, only about ten (10) to twenty (20) milliliters is arterial. Accordingly, the vast majority of the blood within the brain is venous blood (between about fifty-five (55) and about sixty (60) milliliters). This large amount of venous blood provides significant surface area for delivery and transport of oxygen and other nutrients through the venous system. Furthermore, unlike the heart, the venous system of the brain is not a single outlet system and contains many more vessels that are largely interconnected. This unique physiology facilitates the prevention of edema during selective retroperfusion techniques.

At rest and normothermia, the brain of an awake subject typically receives blood flow between about 45 to 60 milliliters per 100 grams of brain tissue per minute at a perfusion pressure of greater than about 70 mmHg. Further, the maximum pressure that cerebral capillaries are normally subjected to is about 30 mmHg with a mean of about 22 mmHg. As a general consideration, under physiologic conditions capillary pressures beyond 25 mmHg can lead to complications such as tissue edema. Similarly, during a retrograde cerebral perfusion ("RCP") procedure, it is conventionally recommended that the RCP pressure does not exceed 25 mmHg. However, because RCP pressure is measured in the large veins, it does not accurately represent the pressure in the related capillary systems. For example, a RCP pressure measuring 25 mmHG within the large veins will be significantly lower in the related capillaries. Accordingly, the conventionally recommended RCP pressure of less than 25 mmHg used in conventional RCP therapies is considered insufficient for opening up the cerebral microvessels and providing an adequate blood supply thereto. Furthermore, conventional RCP pressures are likely to cause maldistribution of blood throughout the brain due, at least in part, to the sudden loss of cerebral perfusion pressure associated with conversion of antegrade to retrograde perfusion, which may lead to the collapse of the cortical veins and an increased resistance to opening of the cerebrovenous vessels. For these reasons a retrograde perfusion pressure of greater than about 25 mmHg may not necessarily cause tissue edema and some clinical reports suggest that maintaining RCP at relatively high perfusion pressures (e.g., greater than about 25 mmHg) appears to be safe, with evidence of good clinical outcomes and no evidence of either cerebral edema or hemorrhage. While the devices, systems and methods described herein subject the cerebral venous system to such higher RCP pressures, characteristics of the devices, systems and methods described herein provide safeguards against overloading the cerebral venous system.

Now referring to FIG. 1, a schematic view of a retroperfusion catheter 10 is shown. As the various embodiments of the catheter 10 will be described in connection with the provision of retrograde cerebral perfusion therapy to a brain, it will be understood that the catheter 10 is not limited to use in connection with the brain and may be applied to any other areas of the body where the characteristics and/or configuration of the catheter 10 may be useful.

The catheter 10 is configured to be placed within a venous vessel and comprises a flexible, elongated tube having a proximal end 12, a distal end 14, and a body 16 having a lumen 18. The catheter 10 may be comprised of any suitable material known in the medical arts and the dimensions of the catheter 10 may vary depending on the particulars of the specific patient or with respect to the vein to be cannulated. For example and without limitation, the catheter 10 may be configured for insertion within the cerebral venous system to facilitate retrograde cerebral perfusion techniques. Furthermore, the catheter 10 may be coated with heparin or any other suitable anti-coagulant such that the catheter 10 may be placed within a vessel for an extended period of time without inhibiting the blood flow therethrough due to coagulation.

As shown in FIG. 1, the catheter 10 may comprise a tapered configuration to facilitate advancement of the distal end 14 of the catheter 10 into the venous capillaries of the cerebrum or any other narrow vessels as may be appropriate. While one example of the tapered configuration of the catheter 10 is shown in FIG. 1, it will be appreciated that the catheter 10 may be configured in any manner, tapered or otherwise, that allows the distal end 14 of the catheter 10 to be advanced through a blood vessel having a decreasing diameter.

The proximal end 12 of the catheter 10 is open and in fluid communication with the lumen 18 of the body 16. The proximal end 12 of the catheter 10 may be configured in any fashion so long as arterial blood is allowed to flow therethrough and into the lumen 18 of the catheter 10. For example, in the at least one embodiment shown in FIG. 1, the proximal end 12 is configured as a female connector comprising a connector ring 22. Similarly, the distal end 14 of the catheter 10 is configured to allow blood within the lumen 18 to flow out of the catheter 10. Accordingly, when the catheter 10 is positioned within a venous vessel and supplied with arterial blood, the oxygenated arterial blood is allowed to flow into the catheter 10 through the proximal end 12, through the lumen 18, and out of the catheter 10 through the distal end 14 (as well as through a plurality of orifices 20 which will be discussed in further detail herein). As this is a retroperfusion technique, it will be understood that the arterial blood being introduced into the vein through the catheter 10 is flowing in a direction retrograde to the normal flow of venous blood.

Figure 2:
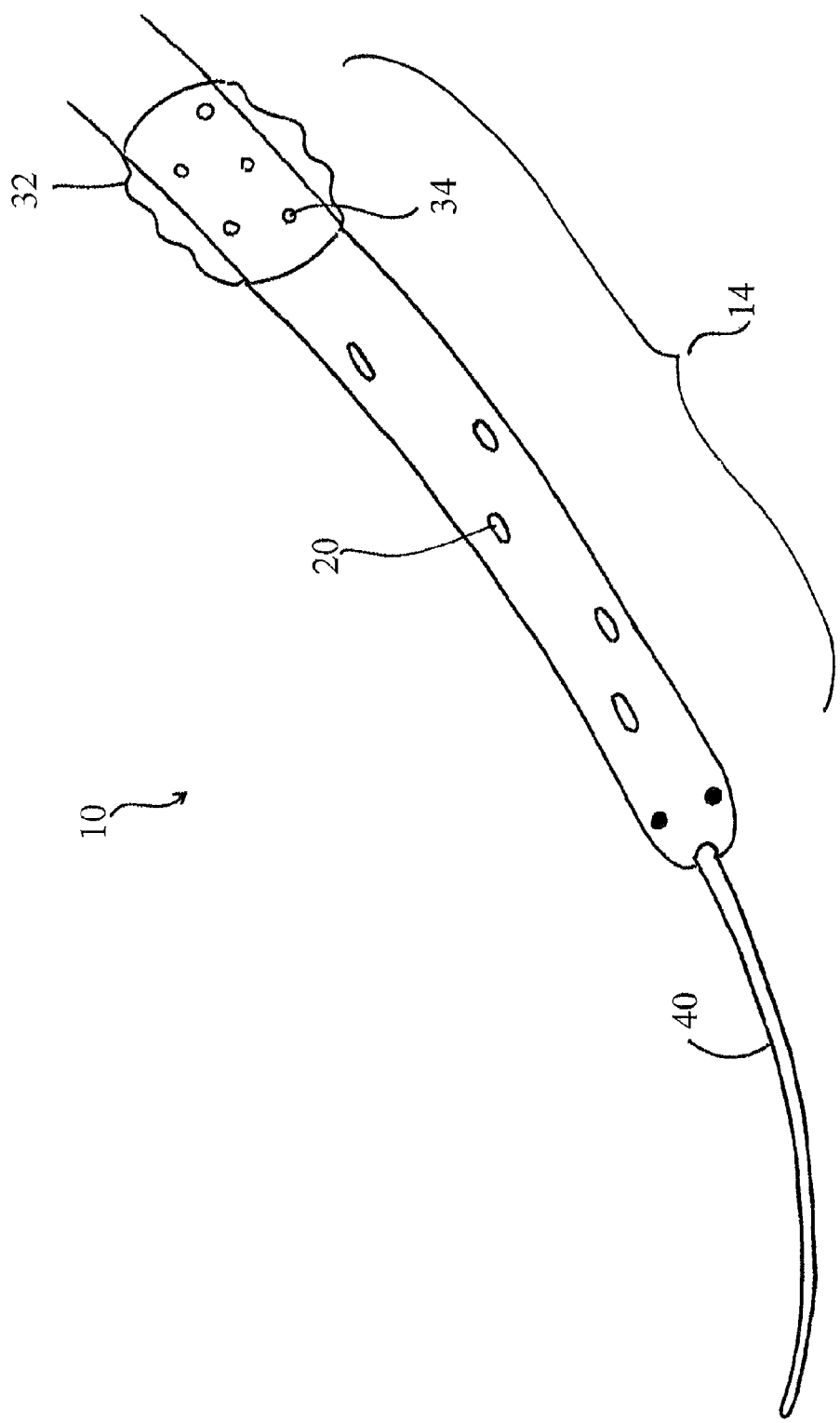
FIG. 2 shows a side view of the distal end of the catheter of FIG. 1.

The distal end 14 of the catheter 10 is further configured such that one or more guidewires 40 positioned within the lumen 18 of the body 16 may be advanced therethrough (see FIG. 2). In addition, the distal end 14 further comprises one or more sensors 24. While the one or more sensors 24 are described herein as being positioned on the distal end 14 of the catheter 10, it will be appreciated that the one or more sensors 24 may be positioned anywhere on the body 16 of the catheter 10.

Among other things, inclusion of the at least one sensor 24 on the catheter 10 can provide information regarding the pressure within the vein into which the catheter 10 is being inserted. In this manner, the at least one sensor 24 can assist a clinician in determining the severity of ischemic damage to an affected area of the brain, as well as whether or not the appropriate pressure drop in the retroperfused arterial blood flow has been achieved upon initiation of the retroperfusion therapy.

The one or more sensors 24 of the distal end 14 may comprise any sensor that may be useful in the medical arts, such as and without limitation, sensors to measure the flow rate within the vein of interest, pressure sensors, and/or sensors for measuring the pH, the partial pressure of carbon dioxide within the vein or oxygen saturation, lactic acid concentration, or temperature of the blood therein. The inclusion of specific type(s) of sensors 24 on the distal end 14 of the catheter 10 may be determined on a case-by-case basis, depending on the particular needs of the patient at issue. For example and without limitation, the at least one sensor 24 comprises a flow sensor to assist a clinician with tailoring the flow rate within the perfused vein to a specific value.

The at least one sensor 24 of the catheter 10 is further capable of transmitting the data collected to an external device. As shown in FIG. 1, one or more of the at least one sensors 24 may be a wired device. In the at least one embodiment shown in FIG. 1, the sensor 24 is coupled with a sensor cable 26 for transmitting the data gathered by the related sensor 24 to a remote module 270 (see FIG. 4). The sensor cable 26 extends through the lumen 18, out of the proximal end 12 of the catheter 10, and is coupled with the remote module 270 that may either be implanted on the patient subcutaneously or positioned remotely. In this manner, the data gathered by each of the at least one sensors 24 can be transmitted through the sensor cable 26 to the remote module 270 such that a clinician can view and/or ascertain the same on a real-time basis or otherwise. Alternatively or additionally, one or more of the at least one sensors 24 may be capable of wirelessly communicating the data it has gathered to the remote module 270 through the use of telemetry technology, the internet, radio waves, or any other wireless means. As such, wireless sensors 24 do not require attachment to the sensor cable 26 and can wirelessly transmit the gathered data to the remote module 270 without being in physical or electrical contact therewith.

The body 16 of the catheter 10 extends between the proximal and distal ends 12, 14 of the catheter 10 and comprises a plurality of orifices 20 disposed along its length. Each of the plurality of orifices 20 are in fluid communication with the lumen 18 of the catheter 10 such that when arterial blood flows through the lumen 18 of the catheter 10, a portion of the blood flows through the plurality of orifices 20 and into the cannulated vein. In this manner, the plurality of orifices 20 of the catheter 10 facilitate the controlled introduction of the oxygen-rich blood into the cerebral venous system.

The specific number, size and placement of the orifices 20 may be determined on a case-by-case basis according to the pressure and/or the flow rate desired within the cerebral venous system. For example and without limitation, if a higher flow rate is desired, the body 16 of the catheter 20 may comprise numerous orifices 20 each having a large diameter. Alternatively, if a lower flow rate is desired, the body 16 of the catheter may not comprise as many orifices 20 and/or each of the plurality of orifices 20 may comprise a small diameter. In a similar fashion, the size, position and number of orifices 20 may also have an affect on the pressure within the cerebral vein in which the catheter 10 is inserted (i.e. the more arterial blood flow that is allowed to flow therein, the higher the pressure within the vein and vice versa).

As shown in FIG. 1, the catheter 10 may further comprise one or more expandable balloons 30, 32 coupled with an intermediary portion of the external surface of the body 16 of the catheter 10 such that each of the expandable balloons 30, 32 encases the catheter 10. In the at least one embodiment of the catheter 10 illustrated in FIG. 1, a first expandable balloon 30 is coupled with the body 16 of the catheter 10 at a first position and a second expandable balloon 32 is coupled with the external surface of the body 16 of the catheter 10 at a second position. The second expandable balloon 32 is positioned distally on the external surface of the body 16 of the catheter 10 relative to the first expandable balloon 30.

Each of the expandable balloons 30, 32 may comprise any expandable balloon that is appropriate for insertion within a vessel and may comprise any material suitable for this function including, without limitation, polyethylene, latex, polyestherurethane, polyurethane, silastic, silicone rubber or combinations thereof. In addition, the at least one balloons 30, 32 may be coated with heparin or any other suitable anti-coagulant such that the at least one expandable balloon 30, 32 may be placed within a vessel without the risk of coagulation. The size and configuration of each expandable balloon will differ between patients and applications. In operation, the at least one expandable balloon 30, 32 can be used to intermittently occlude the vein and prevent the antegrade flow of blood therethrough and anchor the catheter 10 in the desired position within a vessel wall.

The interiors of each of the at least one expandable balloons 30, 32 are in fluid communication with the lumen 18 of the catheter 10. While it will be appreciated that this can be achieved using various different means such as valves, openings or other conduits, in the embodiment shown in FIG. 1, each of the balloons 30, 32 is positioned on the body 16 of the catheter 10 at a location over one or more pores 34 that traverse the external surface of the body 16 and are in fluid communication with the lumen 18 of the catheter 10. Accordingly, as arterial blood flows through the lumen of the catheter, a portion thereof necessarily flows into the interior of each of at least one expandable balloons 30, 32 through the related pores 34. In this manner, each of the balloons 30, 32 is capable of automatically moving from a deflated to an expanded position when blood flows through the lumen 18 of the catheter 10. Likewise, each of the balloons 30, 32 is further capable of automatically moving from the expanded position back to a deflated position when the arterial blood flow through the lumen 18 of the catheter 10 either is not sufficient to maintain the balloons 30, 32 in the expanded position or ceases altogether. In both of these cases, when the pressure is not sufficient to maintain the arterial blood within the interior of the at least one balloon 30, 32, the arterial blood drains back through the at least one pore 34 in the body 16 of the catheter 10 and into the lumen 18 in accordance with the antegrade flow of blood through the venous vessel.

With respect to use of the catheter 10 to provide retrograde cerebral perfusion therapy for treatment of a stroke or otherwise, the proximal end 12 of the catheter 10 is coupled with an arterial blood supply (as will be described in further detail herein) such that the arterial blood is injected into the lumen 18 of the catheter 10 through the proximal end 12 thereof in synchrony with the patient's sinus rhythm. Accordingly, when oxygen-rich arterial blood is pumped in a retrograde fashion into a venous vessel as a result of the systolic contraction of the heart, the expandable balloons 30, 32 of the catheter 10 each expand as the arterial blood flows into the interiors thereof. As the expandable balloons 30, 32 are positioned at different locations along the body 16 of the catheter 10, the first balloon 30 may expand prior to the second balloon 32 depending on the flow rate and pressure of the arterial blood flow moving through the lumen 18 of the catheter 10.

The expansion of the expandable balloons 30, 32 occludes the venous vessel in which the catheter 10 is inserted, prevents the normal antegrade flow of blood through the venous vessel, and increases the pressure therein. In this manner, the oxygen-rich arterial blood that was delivered into the vessel through the plurality of orifices 20 and the distal end 14 of the catheter 10 at a location upstream of the balloon occlusions is forced to remain within the vein for a period of time and perfuse the surrounding capillaries. Accordingly, the occlusion of the vein by the at least one expanded balloon 30, 32 allows the penumbral tissue vascularized by the venous vessel at issue to benefit from the nutrients contained in the arterial blood.

Thereafter, during diastole when the arterial blood is not actively pumped by the heart through the catheter 10, the arterial blood pumped into the catheter 10 (and thus the interiors of the balloons 30, 32) in the previous systolic cycle drains back into the lumen 18 of the catheter 10 through the one or more pores 34. This immediately reduces the pressure within the interiors of the balloons 30, 32 and automatically deflates the same. Due to the placement of the balloons 30, 32 on the body 16 of the catheter 10, the second balloon 32 may deflate or begin deflating before the first balloon 30 due to the flow of arterial blood through the catheter 10 (i.e. in succession). (It will be appreciated that the first and second balloons 30, 32 may expand/deflate in succession or in unison, depending on the forward pressure of the system). In this manner, the expandable balloons 30, 32 no longer occlude the vein and the antegrade flow of blood through the venous vessel resumes. Accordingly, the venous blood and the supplemented arterial blood within the vein is allowed to drain out of the venous vessel in accordance with normal antegrade flow and the pressure within the venous vessel is reduced.

The rate at which the expandable balloons 30, 32 of the catheter 10 automatically move between the expanded and deflated positions can be manipulated pursuant to each of the balloons' 30, 32 pressure to volume ratio and/or the size and number of pores 34 associated therewith. For example, and without limitation, a clinician can manipulate the configuration of either or both of the expandable balloons 30, 32 (i.e. the thickness and/or elasticity of the material comprising the expandable balloons 30, 32 and/or the overall shape and size thereof) to achieve the desired pressure to volume ratio. In this manner, the expandable balloons 30, 32 are capable of automatically expanding at a desired rate and to a desired size when a sufficient pressure is exerted within their interiors by the influx of arterial blood. In addition, the expandable balloons 30, 32 are also capable of automatically deflating at a desired rate when the pressure within the interiors of the balloons 30, 32 falls below a predetermined threshold due to the outflow of arterial blood.

As previously indicated, the configuration of the one or more pores 34 may also be modified to achieve a specific expansion and/or deflation rate. For example, the size and/or number of the pore(s) 34 can be increased if a faster expansion and/or deflation rate is desired, or the pore(s) 34 may be decreased in size and/or number for a slower, more controlled expansion and/or deflation rate. In this manner, a clinician can ensure that the expandable balloons 30, 32 will expand to the appropriate size and deflate therefrom within a desired timeframe and therefore achieve the desired effect.

Figure 3:
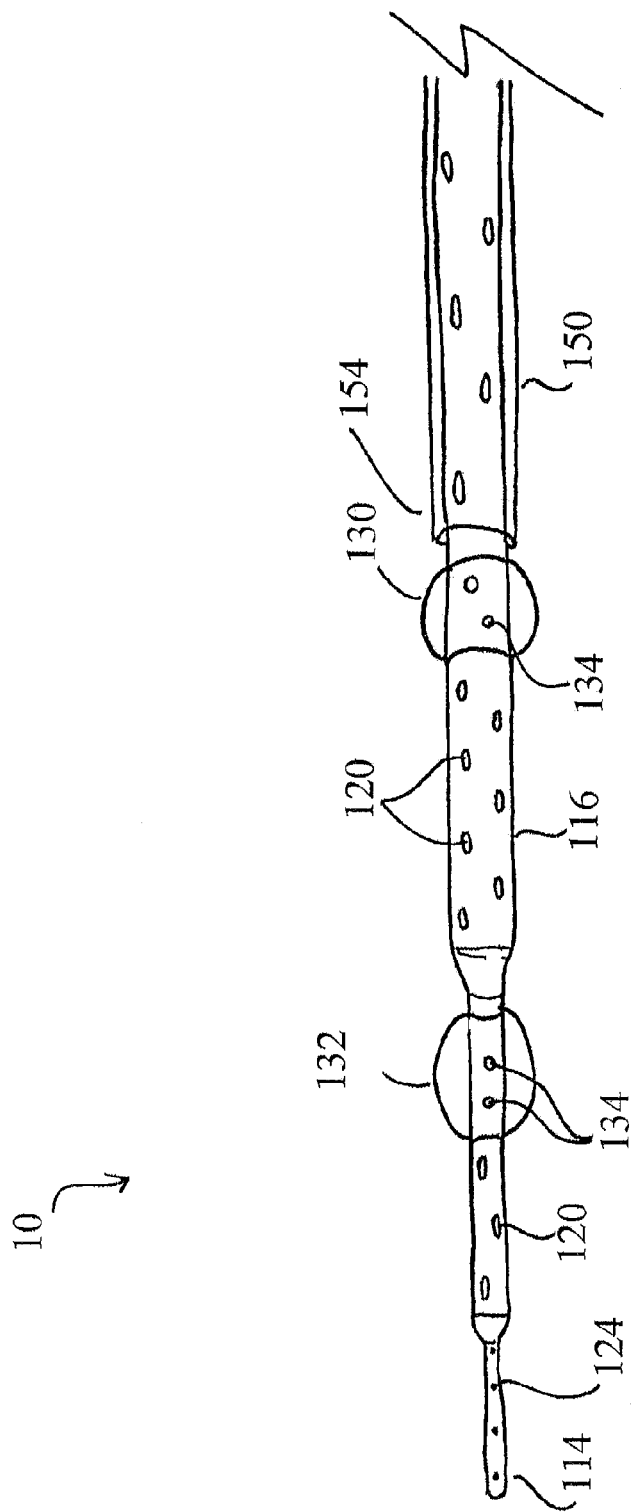
FIG. 3 shows the catheter of FIG. 1 coupled with a sheath.

Now referring to FIG. 3, a side view of at least one alternative embodiment of the catheter 10 is shown. In this at least one embodiment, the catheter 10 further comprises a sheath 150. The sheath 150 is configured to be placed within a venous vessel over the catheter 10 and comprises a semi-flexible, elongated tube having a proximal end (not shown), a distal end 154 and a lumen configured to slidably receive the body 16 of the catheter 10 therein. The sheath 150 may be comprised of any suitable material including, without limitation, polyurethane, poly(tetrafluoroethylene) or silicone rubber. Furthermore, the sheath 150 may be coated with heparin or any other suitable anti-coagulant such that the sheath 150 may be placed within a vessel without inhibiting blood flow due to coagulation.

The dimensions of the sheath 150 may vary depending on the particulars of a specific patient or with respect to the vein to be cannulated, and are directly related to the dimensions of the catheter 10. For example, the diameter of the sheath 150 is such that while the lumen of the sheath 150 is capable of slidably receiving the body 116 of the catheter 110 therein, the sheath 150 is tightly fit around the body 116 of the catheter 10 when the sheath 150 is advanced there over. In this manner, when the sheath 150 is advanced over a portion of the body 116 of the catheter 10, the sheath 150 effectively seals the orifices 120 of the catheter 10 that are positioned there under. In addition, the sheath 150 is also capable of being advanced over the at least one expandable balloons 130, 132 located at various positions on the body 116 of the catheter 10 when the expandable balloons 130, 132 are in the deflated configuration. Accordingly, a clinician can customize the flow of blood into the venous vessel from within the lumen 118 of the catheter 10 by advancing or retracting the sheath 150 to either increase or decrease, respectively, the amount of orifices 120 that are available to allow blood to flow therethrough. In addition, by advancing the sheath 150 over one or more of the at least one balloons 130, 132, a clinician can decrease the number of expandable balloons available to occlude the vein during systole and thereby promote the blood within a particular area of the vein to drain therefrom.

Due to the inherent pressure differences between the arterial and venous systems, one of the main challenges of successfully delivering retroperfusion therapies is that the arterial blood pressure must be reduced prior to being introduced into a vein due to the thinner and more fragile anatomy of the venous walls. Indeed, subjecting a venous vessel to the high pressures of arterial blood flow typically results in rupture of the venous wall. Accordingly, with retroperfusion therapies, it is critical to ensure that the pressure of the arterial blood flow is at least initially controlled such that the venous vessel is not subjected to the unregulated pressure of the arterial blood flow.

Maintaining control of this pressure discrepancy is especially important when retroperfusion therapy is applied to the venous system of a brain. The tight normal range of the brain's intracranial pressure is due, at least in part, to its enclosure within the cranium. Accordingly, even slight deviations in the normal pressure within the brain's venous vessels can result in extremely problematic outcomes. Accordingly, in addition to regulating the amount of blood flow into the ischemic area of the brain, it is also necessary to regulate the pressure of the arterial blood prior to its introduction into the venous system through the catheter 10.

Figure 4:
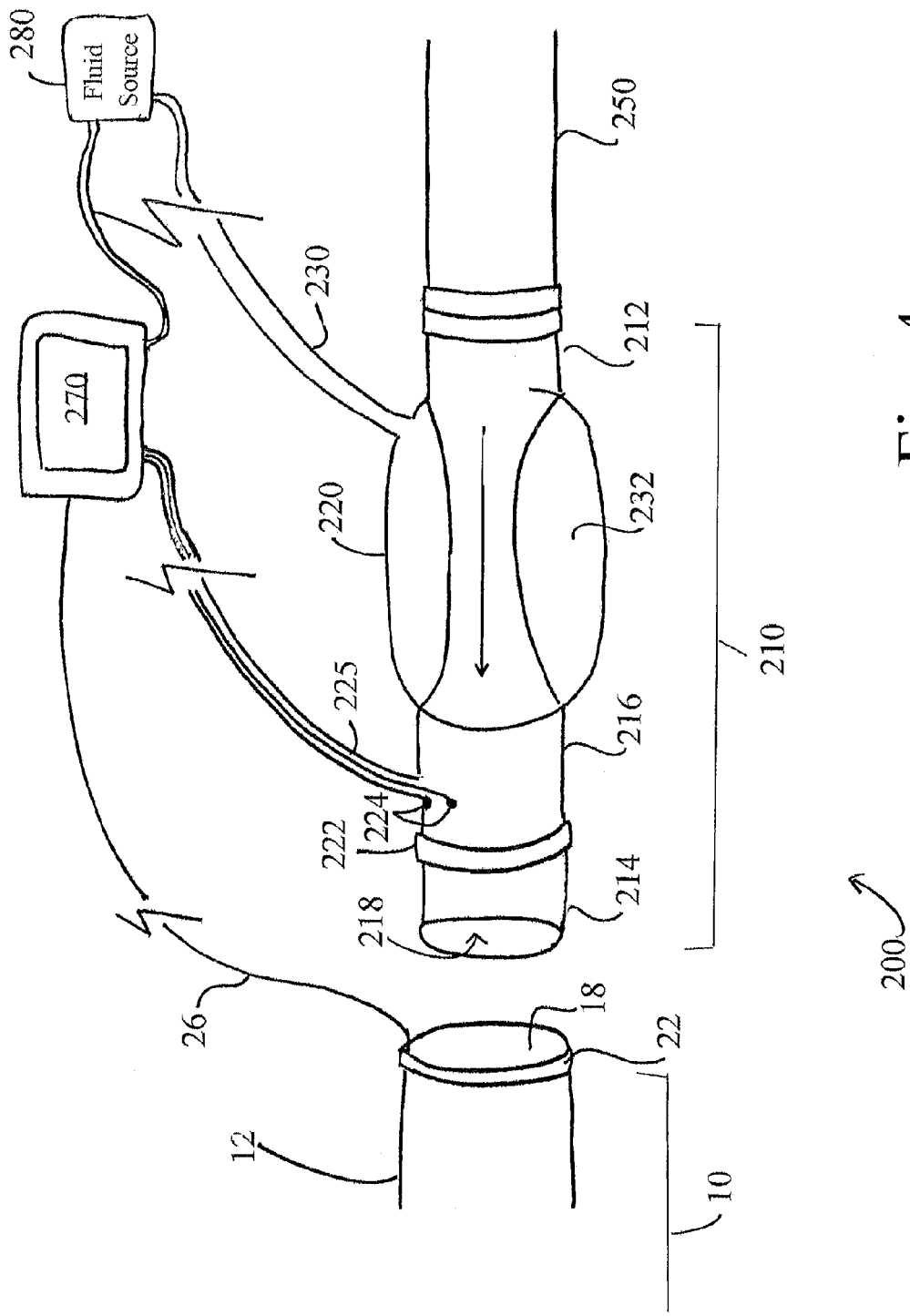
FIG. 4 shows a schematic view of a flow unit for use in connection with the catheter of FIG. 1 to achieve regulation of arterial blood flow and pressure.
Figure 5:
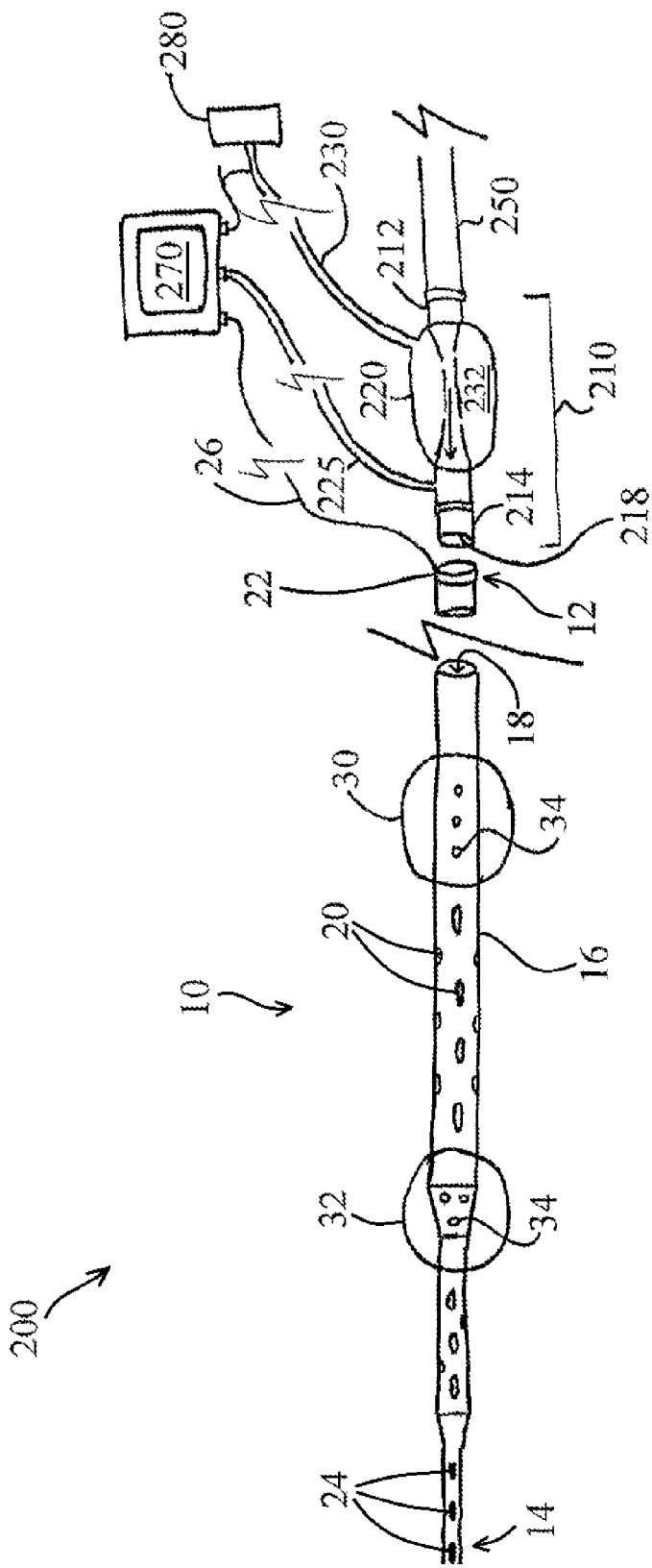
FIG. 5 shows a retroperfusion system for providing a retroperfusion therapy to an ischemic area of a brain.

Now referring to FIGS. 4 and 5, side views of an autoretroperfusion system 200 are shown. With respect to the brain, the autoretroperfusion system 200 may be used in the treatment of stroke and, specifically, as a bridge therapy to extend the viability of the penumbra region of the ischemic brain tissue. As previously described with respect to the catheter 10, the autoretroperfusion system 200 is capable of providing arterial blood flow to an ischemic region of a patient's brain by injecting arterial blood in a controlled manner in synchrony with the patient's sinus rhythm. Furthermore, the autoretroperfusion system 200 is capable of controlling the pressure of the arterial blood flow prior to introducing the same to the venous system of the brain such that when the arterial blood flow is first introduced to the vein, the pressure of the re-routed arterial blood flow is already reduced such that the thinner venous vessels are protected and the blood pressure is maintain within an acceptable pressure range.

As illustrated in FIG. 5, the autoretroperfusion system 200 comprises the catheter 10, a flow unit 210, and a source of arterial blood flow 250. The catheter 10 is for placement within the venous vessel of the brain and is configured as previously described in connection with FIGS. 1-3. The flow unit 210 is configured for use in connection with the catheter 10 and is responsible for regulating the arterial blood pressure prior to its introduction into the catheter 10. The source of arterial blood flow 250 is for placement within an arterial vessel and is configured to re-route at least a portion of the arterial blood flow within the arterial vessel into the autoretroperfusion system 200 and may comprise a catheter or other device as is known in the art.

The flow unit 210 of the autoretroperfusion system 200 is responsible, at least in part, for the regulation of the pressure of the arterial blood flow prior to its introduction into the catheter 10 and ultimately the vein. The flow unit 210 comprises a proximal end 212, a distal end 214, a body 216 extending between the proximal and distal ends 212, 214, a chamber 220, and an interior 218 extending through the chamber 220 and between the proximal and distal ends 212, 214 of the flow unit 210. Both the proximal end 212 and the distal end 214 of the flow unit 210 may comprise any standard catheter materials that are suitable in the medical arts. The proximal end 212 of the flow unit 210 is configured to receive fluid therethrough and to allow such fluid to flow into the interior 218 of the flow unit 210. In addition, the proximal end 212 is configured to securely couple with the source of arterial blood flow 250. The source of arterial blood flow 250 and the proximal end 212 may be coupled in any manner known in the art, provided a secure connection is formed therebetween and arterial blood is allowed to travel from the source of arterial blood flow 250 into the interior 218 of the flow unit 210 through the proximal end 212 thereof.

The distal end 214 of the flow unit 210 comprises an open end and is configured such that arterial blood can flow therethrough. In addition, the distal end 214 of the flow unit 210 is configured to securely couple with the proximal end 12 of the catheter 10. For example and without limitation, the distal end 214 of the flow unit 210 may comprise a male connector having a connector ring 222 such that the distal end 214 of the flow unit 210 can securely mate with the female configuration and connector ring 22 of the proximal end 12 of the catheter 10 (see FIG. 4). When the flow unit 210 is coupled with the source of arterial blood flow 250 and the catheter 10, the arterial blood is allowed to flow into the flow unit 210 through the proximal end 212 thereof, through the interior 218 of the flow unit, and into the lumen 18 of the catheter 10 through the distal end 214 of the flow unit 210.

As shown in FIG. 4, the distal end 214 of the flow unit 210 may further comprise at least one sensor 224 disposed therein. The at least one sensor 224 may be disposed in any location within the distal end 214 of the flow unit 210 so long as the at least one sensor 224 is capable of gathering data on the flow of fluid traveling therethrough. As shown in FIG. 4, in at least one embodiment, the at least one sensor 224 may be disposed on the interior wall of the distal end 214 and/or be tethered to the interior wall of the distal end 214 such that the at least one sensor 224 is floating within the arterial blood flowing through the interior 218 of the flow unit 210.

The at least one sensor 224 may be used for monitoring purposes and is capable of periodically or continuously collecting data from the arterial blood flowing through the interior 218 of the flow unit 210. For example, the at least one sensor 224 may be capable of monitoring the pressure and/or flow rate of the arterial blood flowing through the distal end 214 of the flow unit 210. Additionally, one or more of the at least one sensors 224 may be used to monitor the pH or the concentrations of carbon dioxide, lactate or other compounds within the arterial blood, activating clotting time data, or any other data on the arterial blood that may be useful. The inclusion of specific type(s) of sensors 224 in the distal end 214 of the flow unit 210 may be determined on a case-by-case basis, depending on the particular needs of the patient.

The at least one sensor 224 of the distal end 214 of the flow unit 210 is further capable of transmitting the data collected to an external device. In the at least one embodiment shown in FIG. 4, the at least one sensor 224 is a wired device. In this embodiment, the wire component of the sensor travels through a sensory port 225 to a remote module 270 (which will be described in more detail herein). In this at least one embodiment, the sensory port 225 is configured as an elongated conduit in which the wire of the at least one sensor 224 is encased. Alternatively or additionally, one or more of the at least one sensors 224 may be capable of wirelessly communicating the data it has gathered to the remote module 270 through the use of telemetry technology, the internet, radio waves, or other wireless means, such that the collected data can be easily accessed by a clinician on a real-time basis or otherwise. It will be understood that the flow unit 210 may comprise any number or type of sensors 224 and that each of the at least one sensors 224 may be capable of collecting a specific type or multiple types of data from the arterial blood flowing through the flow unit 210.

The chamber 220 of the flow unit 210 is coupled with the exterior surface of the body 216 of the flow unit 210 and comprises an interior 232 and an exterior cage or surface comprised of any material that is capable of being inflated and deflated. For example and without limitation, in at least one embodiment, the chamber 220 may comprise polyethylene, latex, polyestherurethane, polyurethane, silastic, silicone rubber or combinations thereof. In operation, the chamber 220 can be used to form a temporary stenosis or barrier within the interior 218 of the flow unit 210 in order to reduce the pressure of arterial blood flowing therethrough.

The chamber 220 is capable of being controlled by a clinician, through use of the remote module 270 or otherwise, such that the chamber 220 can inflate and/or deflate to the appropriate size based on the pressure and/or flow rate of the arterial blood flowing through the interior 218 of the flow unit 210. The interior 232 of the chamber 220 is in fluid communication with a fluid source 280 through at least one port 230. Accordingly, the at least one port 230 functions as a conduit through which a fluid supplied from the fluid source 280 (e.g., a gas or a liquid) can be injected into or removed from the interior 232 of the chamber 220. The fluid source 280 may be positioned externally of the patient or may comprise a subcutaneous port through which fluid can be periodically injected and withdrawn.

As shown in FIGS. 4, 5, 6A, and 6B, a portion of the body 216 of the flow unit 210 traverses the center of the chamber 220. As this portion is surrounded by the chamber 220, the external surface of the portion of the body 216 surrounded by the chamber 220 may be in contact any liquid or gas injected into the interior 232 of the chamber 220 and the internal surface of the portion of the body 216 surrounded by the chamber 220 may be in contact with blood flowing through the interior 218 of the flow unit 210.

The portion of the body 216 surrounded by the chamber 220 is comprised of a flexible or semi-flexible membrane such that the chamber 220 acts as a diaphragm with respect to the body 216, and thus the interior 218, of the flow unit 210.

Figure 6A:
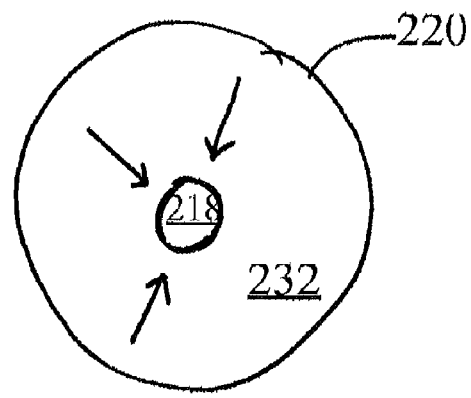
FIGS. 6A and 6B show cross-sectional views of the flow unit of FIG. 4 wherein the chamber thereof is in an inflated configuration (FIG. 6A) and in a deflated configuration (FIG. 6B).
Figure 6B:
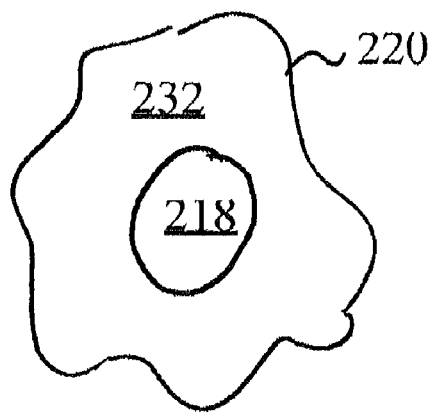

In other words, when the pressure within the interior 232 of the chamber 220 is greater than the pressure within the interior 218 of the flow unit 210 due to the injection of fluid therein or otherwise, the chamber 220 asserts a compressing force on the flexible or semi-flexible walls of the portion of body 216 of the flow unit 210 that is sufficient to decrease the diameter of the underlying interior 218 of the flow unit 210 (see FIG. 6A). In this manner, the chamber 220 is capable of decreasing the size of the interior 218 of the flow unit 210 and thus forming a stenosis therein such that the flow of arterial blood therethrough is inhibited. Conversely, when the pressure within the interior 232 of the chamber 220 is less than the pressure within the interior 218 of the flow unit 210, the body 216 of the flow unit 210 is maintained at its standard diameter and the size of the chamber 220 is unaffected (see FIG. 6B).

By controlling the volume of fluid within the interior 232 of the chamber 220 as a function of time, the flow unit 210 can affect the wave pressure and volume of arterial blood flowing through the interior 218 of the flow unit 210 and out of the distal end 214 thereof into the catheter 10. For example and without limitation, in at least one embodiment, the flow unit 210 is capable of decreasing the pressure and volume of arterial blood flowing through the distal end 214 of the flow unit 218 when a sufficient volume of fluid, such as for example, carbon dioxide, is injected into the interior 232 of the chamber 220 through the at least one port 230. When this occurs, a compressional force is exerted on the portion of the body 216 of the flow unit 210 surrounded thereby such that a temporary stenosis is formed within the underlying interior 218 of the flow unit 210. As the arterial blood flows through the stenosed interior 218 of the flow unit 210, the volume of arterial blood allowed therethrough is necessarily decreased along with the pressure of the arterial blood flowing through the distal end 214 of the flow unit 210. In this manner, the flow unit 210 can achieve the desired pressure drop in the arterial blood flowing between the arterial and venous systems. Furthermore, the stenosis effect of the chamber 220 can be reversed by removing the carbon dioxide or other fluid from the interior 232 of the chamber 220 through the at least one port 230. In this manner, the portion of the interior 218 surrounded by the chamber 220 can return to its original configuration.

Because the venous system of the brain is so sensitive to changes in pressure and flow, it is necessary to counteract the increased arterial flow rate resulting from the arterial blood moving through the stenosis formed by the chamber 220. Accordingly, the autoretroperfusion system 200 is capable of varying the inflation and deflation of the chamber 220 (and therefore the creation and removal of the stenosis effect on the interior 218 of the flow unit 210) as a function of time. For example and without limitation, the volume of the interior 232 of the chamber 220 may be manipulated so as to drive the pressure of the arterial blood flowing through the interior 218 of the flow unit 210 to between about 30 mmHg and about 40 mmHg for a predetermined period of time. Thereafter, the volume of the interior 232 of the chamber 220 may be manipulated such that the pressure of the arterial blood flowing through the interior 218 of the flow unit 210 drops for a predetermined period of time.

Through periodically driving the pressure and/or flow rate of the arterial blood to a higher pressure and thereafter decreasing the same, the autoretroperfusion system 200 can ensure that any stress caused to the venous system by the retrograde arterial blood flow is periodically and consistently relieved, thereby providing the venous system a temporary reprieve to prevent overload. It will further be understood that this periodic manipulation of the arterial blood flow and pressure through use of the flow unit 210 may also be coordinated with the sinus rhythm of the patient. In this manner, not only is the venous system allowed a periodic interruption to the increased pressure and flow rate of the arterial blood, but antegrade blood flow through the venous system may also be allowed to periodically resume, thereby further reducing the overall stress on the system.

The rate at which the chamber 220 of the flow unit 210 is inflated and deflated may be controlled by a remote module 270. The remote module 270 comprises a computer or other processing means, and is capable of receiving the data collected by the sensors 24, 224 of the autoretroperfusion system 200 and causing fluid to be injected into or withdrawn from the interior 232 of the chamber 220. As previously described, the remote module 270 may be coupled with the at least one sensor 224 of the distal end 214 of the flow unit 210 via a wire encased in the sensory port 225 (as shown in FIG. 4) and/or be capable of receiving the data collected from the at least one sensor 224 via wireless transmission. Similarly, the remote module 270 may be coupled with the at least one sensor 24 of the catheter 10 and/or be capable of receiving the data collected from the at least one sensor 24 via wireless transmission. Furthermore, as the remote module 270 may be positioned remotely from the patient, the data gathered by the sensors 24, 224 of the autoretroperfusion system 200 is easily accessible by a clinician.

The remote module 270 is further coupled with the fluid source 280 and is capable of controlling the amount of fluid injected into and withdrawn from the interior 232 of the chamber 220, as well as the intervals at which the same occurs. As previously described, the volume of fluid within the interior 232 of the chamber 220 has a direct affect on the rate and pressure of the arterial blood flowing through the distal end 214 of the flow unit 210. Accordingly, the remote module 270 can control the pressure drop in the arterial blood through manipulation of the fluid volume within the interior 232 of the chamber 220.

In addition, the remote module 270 is configured such that it can be programmed to automatically analyze the data received from the sensors 24, 224 of the autoretroperfusion system 200 and, based on the results thereof, automatically adjust the volume of fluid injected into or withdrawn from the interior 232 of the chamber 220 in order maintain the arterial blood pressure and flow rate within the acceptable pre-programmed parameters. Accordingly, due to the placement of the at least one sensors 24, 224 of the autoretroperfusion system 200, the remote module 270 can quickly calculate the effect that various manipulations of the volume of fluid within the interior 232 of the chamber 220 are having on the flow and pressure of the arterial blood perfusing the venous vessel, and maintain real-time data on the overall effect the retroperfusion therapy is having on the venous system.

In at least one embodiment, the remote module 270 can be driven by an algorithm such that the remote module 270 is capable of executing the inflation and deflation of the chamber 220 of the flow unit 210 pursuant to a set of desired flow parameters, pressure and perfusion rates. In other words, in this at least one embodiment, the remote module 270 utilizes an algorithm to ascertain the optimal flow parameters within the venous vessel based on the data collected from the sensors 24, 224. Thereafter, based upon those parameters, the remote module 270 automatically manipulates the injection of fluid into and the withdrawal of fluid from the interior 232 of the chamber 220 on an interval basis to achieve the arterial blood flow, pressure, and any other criterion of interest within the optimal ranges.

As previously discussed, the remote module 270 can be programmed to perform these functions at reoccurring intervals in order to ensure that the venous system is not being overstressed. For example, in at least one embodiment, the remote module 270 may be programmed to repeat the cycles of maintaining the pressure of the arterial blood flow flowing through the distal end 214 of the flow unit 210 to between about 30 and about 40 mmHg for 5 seconds, followed by an interval of decreased pressure in the arterial blood flow between about 20 to about 25 mmHg for about 5 seconds. In addition, because the remote module 270 is continuously receiving data from the at least one sensors 24, 224 of the autoretroperfusion system 200, the remote module 270 can automatically adjust the fluid volume within the interior 232 of the chamber 230 to ensure the proper pressure, flow rate and/or other parameters of interest are within acceptable levels.

In at least one embodiment of the autoretroperfusion system 200, the components of the system 200 are available in a package. Here, the package may also contain devices to facilitate delivery of the autoretroperfusion system 200 such as venous and arterial access devices, a delivery catheter, one or more guidewires 40, or any other devices or materials that may be required to administer the autoretroperfusion system 200 appropriately.

Figure 7:
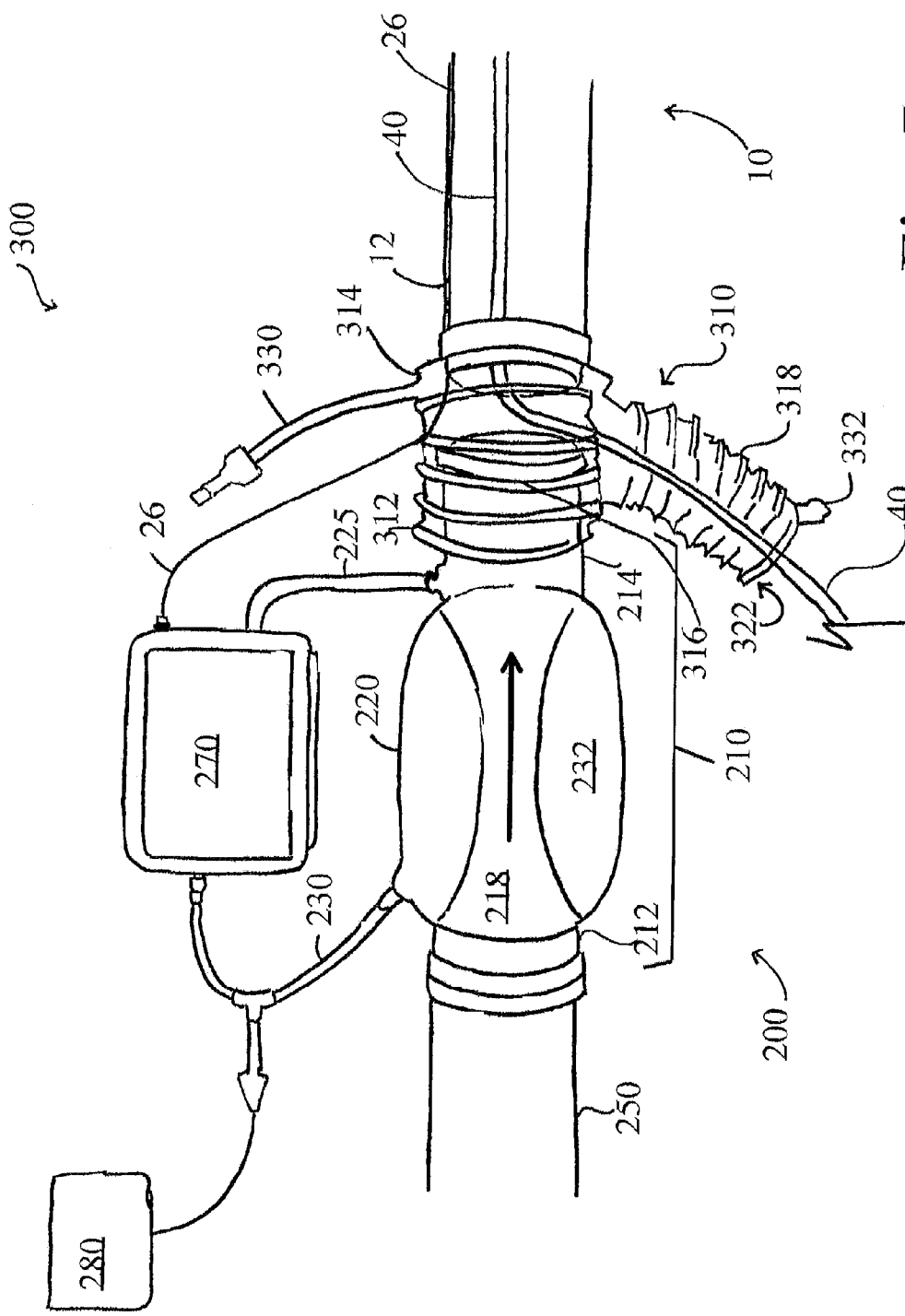
FIG. 7 shows a schematic view of the retroperfusion system of FIG. 5 further comprising a connection assembly.

Now referring to FIG. 7, a schematic view of an autoretroperfusion system 300 is shown. With respect to the brain, the autoretroperfusion system 300 may be used in the treatment of a stoke and, specifically, as a bridge therapy to extend the viability of the penumbra region of the ischemic brain tissue. As previously described with respect to the catheter 10, the flow unit 210, and the autoretroperfusion system 200, the autoretroperfusion system 300 is capable of providing arterial blood flow to an ischemic region of a patient's brain by injecting arterial blood in a controlled manner in synchrony with the patient's sinus rhythm. Furthermore, the autoretroperfusion system 300 is capable of controlling the pressure of the arterial blood flow as it enters the venous vessel of the brain such that when the arterial blood flow is first introduced to the venous system, the pressure of the re-routed arterial blood flow is reduced to protect the thinner venous vessels and maintain the same within an acceptable pressure range. In addition, the autoretroperfusion system 300 is capable of providing a sterile environment for the initial implantation and connection of the underlying components of the autoretroperfusion system 300 and provides a mechanism for reducing the risk of air embolism resulting from the procedure.

As illustrated in FIG. 7, the autoretroperfusion system 300 comprises the catheter 10, the flow unit 210, the source of arterial blood flow 250, and a connection assembly 310. The catheter 10 is for placement within the venous vessel of the brain and is configured as previously described in connection with FIGS. 1-3. The flow unit 210 is likewise for coupling the source of arterial blood flow 250 with the catheter 10 and is responsible for regulating the arterial blood flow and pressure prior to its introduction into the catheter 10, and is configured as previously described in connection with FIGS. 4-6B. The source of arterial blood flow 250 is for placement within an arterial vessel and is configured previously described in connection with the autoretroperfusion system 200. Finally, the connection assembly 310 is for providing a sterile environment within which to connect the components of the system 300 and to ensure that no harmful particulates or gases contaminate the arterial blood flow being perfused into the vein of interest.

The connection assembly 310 comprises a corrugated, sterile bag that is capable of securely coupling with both the distal end 214 of the flow unit 210 and the proximal end 12 of the catheter 10. In at least one embodiment, the connection assembly 310 may be comprised of a transparent plastic material; however, it will be appreciated that the connection assembly 310 may be formed of any flexible or semi-flexible material that is capable of maintaining a sterile environment and coupling with both the flow unit 210 and the catheter 10 in a manner such as to facilitate the flow of fluid therebetween.

The connection assembly 310 comprises a proximal end 312, a distal end 314, a body 316 extending between the proximal and distal ends 312, 314, and a limb component 318 extending from the body 316. Both the body 316 and the limb component 318 of the connection assembly 310 further comprise interiors 320, 322, respectively, and the interior 320 of the body 316 is in fluid communication with the interior 322 of the limb component 318. The limb component 318 of the connection assembly 310 extends from the body 316 of the connection assembly 310 as shown in FIG. 6, and the interior 322 thereof is configured to slidably receive the one or more guidewires 40 that may be used to facilitate advancement and placement of the distal end 14 of the catheter 10.

In addition to the aforementioned, the connection assembly 310 further comprises at least one flushing port 330 and at least one drainage valve 332. The at least one flushing port 330 may be positioned in any location on the connection assembly 310 and is in fluid communication with the interior 320 of the body 316 of the connection assembly 310. Further, the at least one flushing port 330 is additionally coupled with a gas supply (not shown) such that a gas may be injected through the at least one flushing port 330 and into the interior 320 of the connection assembly 310. For example, and without limitation, the at least one flushing port 330 may be coupled with a gas supply containing carbon dioxide.

Furthermore, the at least one flushing port 330 can be used in various capacities in connection with the autoretroperfusion system 300. For example, and without limitation, upon placement of the system 300 within a body, the interiors 320, 322 of the body 316 and limb component 318 of the connection assembly 310 may be continuously flushed with an aseptic gas to create a clean environment. In this manner, the proximal end 12 of the catheter 10 and the distal end 214 of the flow unit 210 may be connected within the aseptic interior 320 of the connection assembly 310, thereby reducing the risk of introducing harmful microbes or other matter into the venous system of the brain as a result of implanting the catheter 10 therein. Moreover, using a resorbable gas, such as carbon dioxide, to flush the system 300 can also provide the added benefit of reducing the risk of air bubbles from entering the system and producing an air embolism.

The at least one drainage valve 332 comprises any one-way valve known in the art and is in fluid communication with at least the interior 320 of the body 316. As shown in FIG. 7, the at least one drainage valve 332 may also be in fluid communication with the interior 322 of the limb component 318. The at least one drainage valve 332 of the autoretroperfusion system 300 automatically allows for any excess gas that is injected into the system 300 through the at least one flushing port 330 or otherwise to be drained therefrom in a sterile and noninvasive manner. As described in the at least one example where an aseptic gas is pumped into the system 300 through the at least one flushing port 330 to provide a sterile environment in which the flow unit 210 and the catheter 10 may be connected, when the pressure within the interior 320, 322 of the connector assembly 310 begins to increase due to the presence of the aseptic gas therein, the excess gas is automatically drained through the at least one drainage valve 332 such that the gas added through the at least one flushing port 330 does not affect the overall pressure of the system 300. The at least one drainage valve 332 may be located outside of the body such that the excess gas drains directly into the environment or, when the connection assembly 310 is implanted at a location within the patient's body, the excess gas can drain from the at least one drainage valve 332 into a conduit that routes the gas to the external environment.

In operation, the connection assembly 310 is fitted over the distal end 214 of the flow unit 210 and the proximal end 12 of the catheter 10 and forms a leak-free attachment with both components 10, 210. In the at least one embodiment where the catheter 10 has been advanced over at least one guidewire 40 to facilitate the proper placement of the distal end 14 thereof, the proximal end of the at least one guidewire 40 may be threaded through the distal end 314 and limb component 318 of the connection assembly 310 such that the at least one guidewire 40 can be manipulated by a clinician with the connection assembly 310 securely in place. Furthermore, prior to coupling the distal end 214 of the flow unit 210 and the proximal end 12 of the catheter 10 to allow the arterial blood to flow therethrough, the at least one flushing port 330 may be used to infuse the interior 320 of the connection assembly 310 with a gas to ensure a sterile environment and any excess gas can be drained through the at least one drainage valve 322. In this manner, the connection assembly 310 is capable of supplying an aseptic and air-free environment in which the flow unit 210 and the catheter 10 may be securely connected, thereby reducing the risk of air embolism or contamination resulting from the procedure.

In at least one embodiment of the autoretroperfusion system 300, the components of the system 300 are available in a package. Here, the package may also contain devices to facilitate delivery of the autoretroperfusion system 300 such as venous and arterial access devices, a delivery catheter, one or more guidewires 40, or any other devices or materials that may be required to administer the autoretroperfusion system 300 appropriately.

Figure 8:
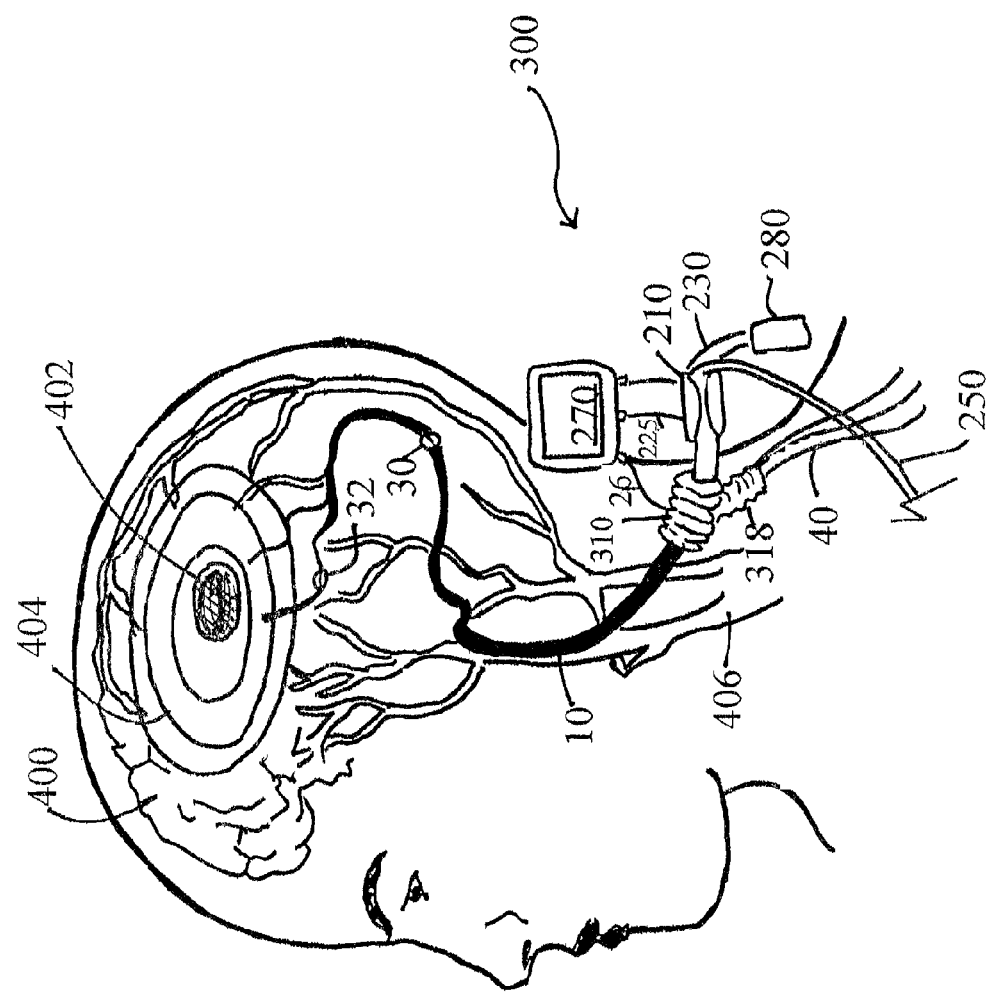
FIG. 8 shows a side view of the retroperfusion system of FIG. 7 as applied to a brain.
Figure 9:
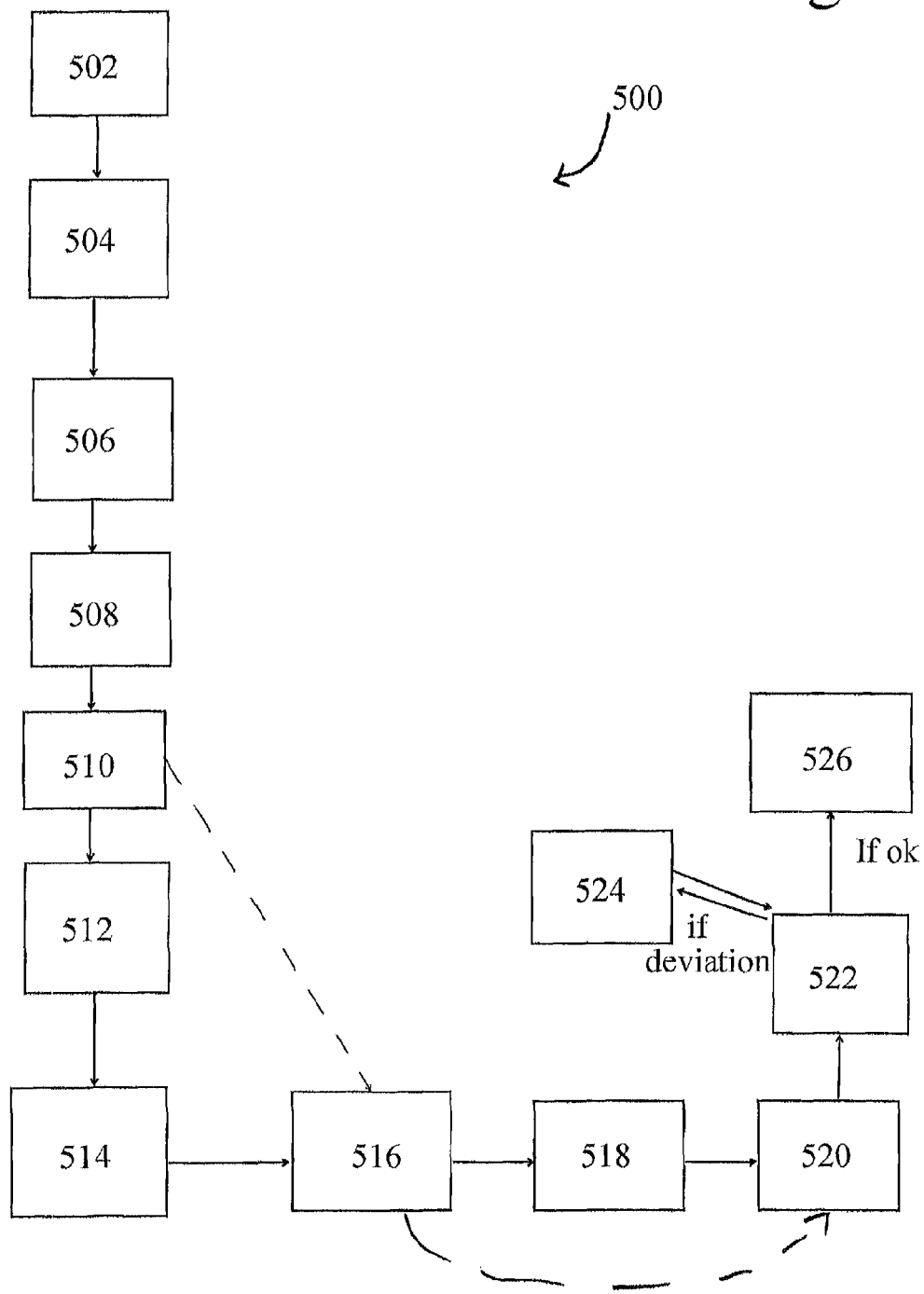
FIG. 9 shows a flow chart of a method for laparoscopically delivering the retroperfusion system of FIG. 7 to a targeted cerebral vein in order to provide retroperfusion therapy thereto.

Now referring to FIG. 8, a side view of the retroperfusion system 300 is shown applied to the brain 400 of a patient in order to facilitate the treatment of a stroke. In addition, FIG. 9 shows a flow chart of a method 500 for performing automatic retroperfusion on a brain using the autoretroperfusion system 300. For ease of understanding, the steps of the method 500 described herein will be discussed relative to the components of the retroperfusion system 300, but it will be appreciated by one skilled in the art that any similar devices and/or systems can be used to perform this method 500. In addition, while the retroperfusion system 300 and the method 500 are described in connection with treating an ischemic area of a brain through catheterization of a venous vessel extending into a penumbral area of a brain, it will be understood that the retroperfusion systems 200, 300 and the method 500 described herein may be applied to perform autoretroperfusion on any organ or tissue in need of retroperfusion treatment.

In at least one approach to the method 500, at step 502, a topographic image of the ischemic area of the brain 400, including the core ischemic infarct 402 and the ischemic penumbra 404, is created using conventional imaging techniques such as magnetic resonance imaging and/or x-ray computer tomography. In this manner, a clinician can determine the location of the ischemic infarct 402 and the penumbra 404 based on cerebral blood flow characteristics and the blood volume within the different areas of the brain 400. At step 504 an artery of interest (not shown) is percutaneously punctured under local anesthesia with a conventional artery access device or as otherwise known in the art. For example and without limitation, in at least one embodiment, an 18 gauge needle is inserted into the desired artery and the source of arterial blood flow 250 is positioned within the artery such that a portion of arterial blood is re-routed therethrough, driven by the pulsatile rhythm of the beating heart. Here, the desired artery may comprise the femoral artery, the subclavian artery, the brachial artery, the radial artery, or any other artery that may be appropriate with respect to the particular patient and/or application.

At step 506, a vein of interest 406 is percutaneously punctured under local anesthesia with a conventional venous access device or as otherwise known in the art. For example and without limitation, in at least one embodiment, an 18 gauge needle is inserted into the jugular vein (labeled as vein 406 in FIG. 9). It will also be appreciated that any other vein may be utilized, provided the vein facilitates retroperfusion of the arterial blood to the desired area of the body. After the vein 406 has been punctured, at step 508, a soft guidewire 40 is inserted into the opening in the vein 406 and advanced into the penumbra region 404 of the brain 400. This may be facilitated through use of the brain topographic imaging taken at step 502 and/or through x-ray (i.e. fluoroscopy) or other suitable visualization techniques.

After the distal end of the guidewire 40 is positioned in the desired location within the penumbra 404 of the brain 400, the distal end 14 of the catheter 10 is inserted into the vein 406 following the guidewire 40 at step 510. Specifically, the distal end 14 of the catheter 10 is threaded over the guidewire 40, inserted into the vein 406 and advanced along the main venous system to the target area within the penumbra 404. Step 510 may be performed under fluoroscopic control or with the aide of other visualization techniques known in the art. Thereafter, the guidewire 40 may optionally be withdrawn from the body through the lumen 18 of the catheter 10 at step 512.

At step 514, the connection assembly 310 is coupled with the proximal end 12 of the catheter 10 and the distal end 214 of the flow unit 210 (see FIG. 7). The connection assembly 310 is fitted over the distal end 214 of the flow unit 210 and the proximal end 12 of the catheter 10 and forms a leak-free attachment with both components 10, 210. Furthermore, in the at least one embodiment of the method 500 where the at least one guidewire 40 was not withdrawn from the patient's body at step 512, the proximal end of the at least one guidewire 40 is threaded through the distal end 314 and the limb component 318 of the connection assembly 310 such that the at least one guidewire 40 extends through the interior 322 of the limb component 318 as illustrated in FIGS. 7 and 8.

At step 516, the flow unit 210 is coupled with the source of arterial blood flow 250 and begins to receive arterial blood flow from the punctured artery within the interior 218 thereof. In this manner, the arterial blood re-routed from the artery of interest (not shown) by the source of arterial blood flow 250 is allowed to flow through the source of arterial blood flow 250 and into the proximal end 212 of the flow unit 210 in a pulsatile fashion pursuant to the rhythm of the patient's heartbeat.

After the proximal end 12 of the catheter 10 and the distal end 214 of the flow unit 210 are positioned within the interior 320 of the connection assembly 310 at step 514, at step 518 the connection assembly 310 initiates the injection of gas into the interiors 320, 322 of the body 316 and the limb component 318. Specifically, the clinician may facilitate the injection of a sterile gas into the interiors 320, 322 of the connection assembly 310 through the at least one flushing port 330 such that the interiors 320, 322 are continuously flushed with the sterile gas. Concurrently, the excess gas injected into the interiors 320, 322 is automatically drained from the connection assembly 310 through the at least one drainage valve 332 of the connection assembly 310. In addition, at step 518, if the at least one guidewire 40 has not previously been withdrawn from the patient's body through the lumen 18 of the catheter 10 at step 512, the at least one guidewire 40 is now removed from the patient through the limb component 318 of the connection assembly 310.

In at least one embodiment of the method 500, the gas injected into the interiors 320, 322 of the connection assembly 310 comprises carbon dioxide. The use of carbon dioxide to flush the autoretroperfusion system 300 ensures that the environment within the connection assembly 310 is aseptic and free of contaminants and/or air bubbles. In this manner, the coupling of the proximal end 12 of the catheter 10 with the distal end 214 of the flow unit 210 can occur within an aseptic, sterile environment, under continuously flowing carbon dioxide (or other gas), and further reduce the risk of adding air to the vein 406 during the connection of the components 10, 210. Accordingly, the sterile environment greatly reduces the risk that any harmful microbes or other matter will be introduced into the venous system of the brain as well as the risk of producing an air embolism within the vein 406 as a result of the therapy applied by the autoretroperfusion system 300.

At step 520, the distal end 214 of the flow unit 210 and the proximal end 12 of the catheter 10 are securely coupled with one another as shown in FIG. 8. Accordingly, the arterial blood from the artery of interest (not shown) is pumped in synchrony with the patient's sinus rhythm through the source of arterial blood flow 250 and into the flow unit 210 wherein the pressure and flow of the arterial blood is regulated by the remote module 270 through use of the chamber 220. Thereafter, the arterial blood having pressure and flow values falling within the appropriate ranges flows into the lumen 18 of the catheter 10 where the arterial blood is perfused in a retrograde fashion into the vein 406 at a target location within the penumbra region 404 of the brain 404. Accordingly, step 520 further comprises the initial inflation and deflation of the chamber 220 of the flow unit 210 as controlled by the remote module 270, and the initial expansion and deflation of the at least one expandable balloons 30, 32 of the catheter 10 in accordance with the systolic and diastolic cycles of the patient's sinus rhythm. In addition, due to the pulsatile nature of the sinus rhythm, the vein 406 is concurrently allowed to drain the excess blood during the diastolic cycle of the sinus rhythm.

At step 522, the remote module 270 assesses whether or not the data measured by the at least one sensors 24, 224 of the catheter 10 and the flow unit 210 fall within the acceptable, pre-programmed ranges. For example, the remote module 270 may be programmed to take into account the arterial blood pressure at the distal end 214 of the flow unit 210 during both diastole and systole, the pressure within the vein 406 as the distal end 14 of the catheter 10 during diastole and systole, the flow rate of the arterial blood through the autoretroperfusion system 300 during diastole and systole, or any other types of information that may assist with the regulation and delivery of the retroperfusion therapy.

In the event the remote module 270 detects any deviation in the data falling outside of the predefined allowable ranges, the method 500 proceeds to step 524. At step 524, the remote module 270 makes adjustments to the autoretroperfusion system 300 until the data received from the sensors 24, 224 indicates that the deviation has been corrected and the data falls within the acceptable parameters. For example, the remote module 270 may adjust the rate of injection and/or withdrawal of fluid from the chamber 220 through the at least one port 330. Additionally or alternatively, the remote module 270 may adjust the volume of fluid injected or withdrawn from the interior 232 of the chamber 220. Accordingly, at step 524, the remote module 270 automatically adjusts the flow and/or pressure of the arterial blood flowing through the flow unit 210 pursuant to the continuous stream of data received from the at least one sensor 24 of the catheter 10 and the at least one sensor 224 of the flow unit 210.

When, either at step 522 or step 524, the remote module 270 verifies that all of the data parameters are in order, the method 500 advances to step 526. At step 526, the remote module 270 defines an arterial blood pressure and flow time cycle based on the data the remote module 270 continuously receives from the at least one sensor 24 of the distal end 14 of the catheter 10 and the at least one sensor 224 of the distal end 214 of the flow unit 210. After the remote module 270 has defined the pressure and flow time cycle, the remote module 270 establishes the same through the interval operation of the fluid source 280 and inflation and/or deflation of the chamber 220. In this manner, the autoretroperfusion system 300 delivers continuous autoretroperfusion therapy to the penumbra 404 of the brain 400 such that the cells within the penumbra 404 can be maintained for an extended period of time following an acute stroke event.

The retroperfusion system 300 will continue to cycle driven by the remote module 270 either until a clinician discontinues the autoretroperfusion therapy, or until the data collected by the at least one sensors 24, 224 and transmitted to the remote module 270 indicates that a deviation has occurred in one of the measured parameters that falls outside of the acceptable range. In the event the latter occurs, the method 500 will revert to step 524 such that the remote module 270 makes adjustments to the injection and/or withdrawal of fluid from the chamber 220 until the data received from the sensors 24, 224 indicates that the deviation has been corrected and the data collected all falls within the acceptable parameters. Upon correction of the deviation, the method 500 again will return to step 526.

The autoretroperfusion system 300 and the method 500 enable a clinician to provide a bridge retroperfusion therapy to a patient suffering from a stoke in order to extend the window of viability of the penumbra 406 of a brain 400 following stroke onset. Accordingly, because the system 300 and method 500 extends the timeframe in which the penumbra 406 is viable, the opportunity to effectively use thrombolytic, neuroprotective, and/or other pharmaceutical agents with respect to the treatment of a stroke is created.

For example and without limitation, in at least one embodiment of the method 500, a clinician may, at step 526, administer one or more pharmaceutical therapies to the patient in conjunction with the retrograde cerebral perfusion therapy provided at this step 526 by the system 300. By continuously providing a controlled arterial blood supply to the penumbra 404, the method 500 and the autoretroperfusion system 300 enables the pharmaceutical agents to establish the appropriate pharmacological concentrations within the area of interest and thereby effectively attack the underlying cause of the stroke (i.e. the clot). Accordingly, use of the method 500 and the retroperfusion system 300 enables not only the provision a successful bridge retroperfusion therapy capable of minimizing cell death within the penumbra 406, but also allows for the extension of time during which alternative treatments, such as prophylactic and/or pharmacological therapies, can be administered in order to further improve efficacy of treatment and reduce associated complication rates.

It will be appreciated that the method 500 may also be employed to deliver the autoretroperfusion system 200. Accordingly, it will be understood that all references to the system 300 in connection with the method 500 may be interchanged with the system 200; however, in this at least one embodiment, the method 500 may omit steps 514 and 518 altogether as the autoretroperfusion system 200 does not comprise the connection assembly 310.

Figure 10:
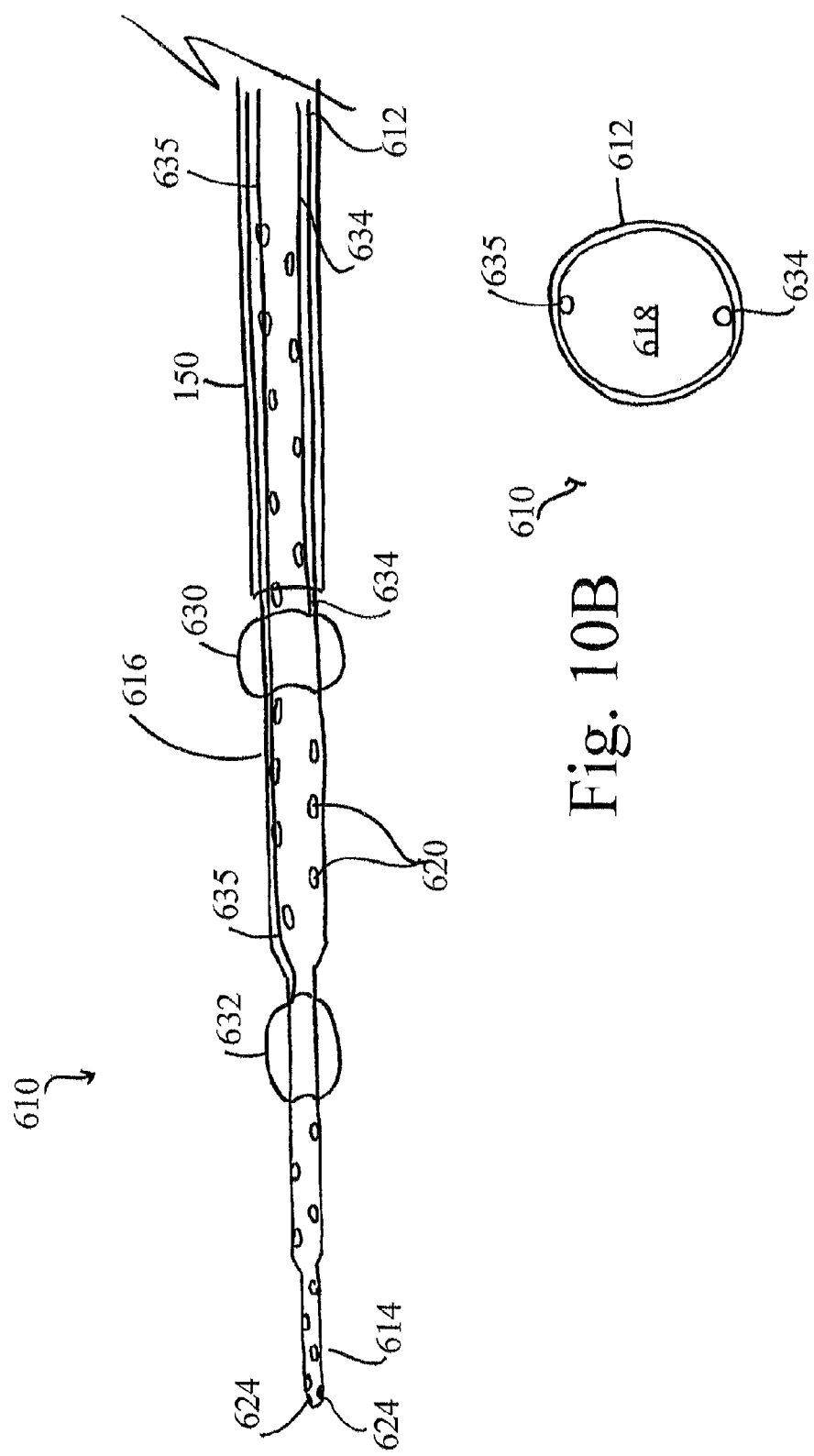
FIG. 10A shows a side view of at least one embodiment of a catheter for delivering arterial blood within a venous vessel.
FIG. 10B shows a cross sectional view of the distal end of the catheter of FIG. 10A.

Now referring to FIG. 10A, a schematic view of a retroperfusion catheter 610 is shown. The catheter 610 is configured similarly to the catheter 10, except with respect to the expandable balloons. As the various embodiments of the catheter 610 will be described in connection with the provision of retrograde cerebral perfusion therapy to a brain, it will be understood that the catheter 610 is not limited to use in connection with the brain and may be applied to any other areas of the body where the characteristics and/or configuration of the catheter 610 may be useful.

Similar to the catheter 10, the catheter 610 is configured to be placed within a venous vessel and comprises a flexible, elongated tube having a proximal end 612, a distal end 614, and a body 616 having a lumen 618. The catheter 610 may be comprised of any suitable material known in the medical arts and the dimensions of the catheter 610 may vary depending on the particulars of the specific patient or with respect to the vein to be cannulated. For example and without limitation, the catheter 10 may be configured for insertion within the cerebral venous system to facilitate retrograde cerebral perfusion techniques. Furthermore, the catheter 610 may be coated with heparin or any other suitable anti-coagulant such that the catheter 610 may be placed within a vessel for an extended period of time without inhibiting the blood flow therethrough due to coagulation.

As shown in FIG. 10A, the catheter 610 comprises a tapered configuration to facilitate advancement of the distal end 614 of the catheter 610 into the venous capillaries of the cerebrum or any other narrow vessels as may be appropriate. While one example of the tapered configuration of the catheter 610 is shown in FIG. 10A, it will be appreciated that the catheter 610 may be configured in any manner, tapered or otherwise, that allows the distal end 614 of the catheter 610 to be advanced through a blood vessel having a decreasing diameter. The proximal end 612, the distal end 614, the body 616 and the lumen 618 of the catheter 610 are all configured identically to the related components of the catheter 10.

The body 616 of the catheter 610 extends between the proximal and distal ends 612, 614 of the catheter 610 and comprises a plurality of orifices 620 disposed along its length. Each of the plurality of orifices 620 are identical to the plurality of orifices 20 described in connection with catheter 10 and, similar to the orifices 20, facilitate the controlled introduction of oxygen-rich arterial blood flowing through the lumen 618 of the catheter 610 and into the cerebral venous system. Similar to the orifices 20 of the catheter 10, the size, number and placement of the orifices 620 may be manipulated to affect the pressure and/or flow rate of the arterial blood flowing therethrough and into the venous system.

Similar to the distal end 14 of the catheter 10, the distal end 614 of the catheter 610 comprises one or more sensors 624 disposed therein or thereon. While the one or more sensors 624 are described herein as being positioned on the distal end 614 of the catheter 610, it will be appreciated that the one or more sensors 624 may be positioned anywhere on or within the body 616 of the catheter 610.

Among other things, inclusion of the at least one sensor 624 on the catheter 610 can provide information regarding the pressure within the vein into which the catheter 610 is being inserted. In this manner, the at least one sensor 624 can assist a clinician in determining the severity of ischemic damage to an affected area of the brain, as well as whether or not the appropriate pressure drop in the retroperfused arterial blood flow has been achieved upon initiation of the retroperfusion therapy.

The one or more sensors 624 of the distal end 614 may comprise any sensor that may be useful in the medical arts, such as and without limitation, sensors to measure the flow rate within the vein of interest, pressure sensors, and/or sensors for measuring the pH, the partial pressure of carbon dioxide within the vein or oxygen saturation, lactic acid concentration, or temperature of the blood therein. The inclusion of specific type(s) of sensors 624 on the distal end 614 of the catheter 610 may be determined on a case-by-case basis, depending on the particular needs of the patient at issue. In addition, each of the at least one sensor 624 of the distal end 614 of the catheter 610 may be configured as discussed with respect to the at least one sensor 24 of the distal end 14 of the catheter 10 and is capable of transmitting the data collected thereby to an external device (either through wired or wireless transmission). Accordingly, similar to at least one embodiment of the at least one sensor 24 of the catheter 10, each of the at least one sensors 624 may optionally be coupled with a sensor cable 626 (see FIG. 11) that is coupled with the remote module 270 (not shown). Furthermore, as described in connection with the catheter 10, the catheter 610 may similarly be used in conjunction with the sheath 150 to assist in the manipulation of the flow of arterial blood out of the plurality of orifices 620 of the catheter 610 and into the vein.

As shown in FIG. 10A, the catheter 610 may further comprise one or more expandable balloons 630, 632 coupled with the external surface of the body 616 of the catheter 610 such that each of the at least one expandable balloons 630, 632 encases the catheter 610. In the at least one embodiment of the catheter 610 illustrated in FIG. 10A, a first expandable balloon 630 is coupled with the body 616 of the catheter 610 at a first position and a second expandable balloon 632 is coupled with the external surface of the body 616 at a second position. Furthermore, the second expandable balloon 632 is positioned distally on the external surface of the body 616 relative to the first expandable balloon 630.

Each of the at least one expandable balloons 630, 632 may comprise any expandable balloon that is appropriate for insertion within a vessel and may be formed of any material suitable for this function including, without limitation, polyethylene, latex, polyestherurethane, polyurethane, silastic, silicone rubber or combinations thereof. In addition, the at least one balloons 630, 632 may be coated with heparin or any other suitable anti-coagulant such that the at least one expandable balloons 630, 632 may be placed within a vessel without the risk of coagulation. The size and configuration of each expandable balloon will differ between patients and applications. In operation, similar to the balloons 30, 32 of the catheter 10, the at least one expandable balloon 630, 632 can be used to intermittently occlude the vein and prevent the antegrade flow of blood therethrough and anchor the catheter 610 in the desired position within a vessel wall.

However, unlike the at least one balloons 30, 32 of the catheter 10, in this at least one embodiment the balloons 630, 632 of the catheter 610 are not capable of automatically expanding and deflating. Accordingly, the interiors of each of the at least one expandable balloons 630, 632 are not in fluid communication with the lumen 618 of the catheter 610. Alternatively, in the at least one embodiment shown in FIGS. 10A and 10B, the interior of the first expandable balloon 630 is in fluid communication with a first balloon port 634, and the interior of the second expandable balloon 632 is in fluid communication with a second balloon port 635. Accordingly, each of the balloons 630, 632 may be expanded or deflated independently upon the injection or withdrawal of fluid therefrom through the respective balloon port 635.

As with the catheter 10, expansion of the at least one expandable balloon 630, 632 of the catheter 610 occludes the venous vessel in which the catheter 610 is inserted, prevents the normal antegrade flow of blood through the venous vessel, and increases the pressure therein. In this manner, oxygen-rich arterial blood delivered into the vessel through the plurality of orifices 620 and the distal end 614 of the catheter 610 at a location upstream of the balloon occlusions is forced to remain within the vein for a period of time and perfuse the surrounding capillaries. Accordingly, occlusion of the vein by the at least one expandable balloon 630, 632 of the catheter 610 allows the penumbral tissue vascularized by the venous vessel at issue to benefit from the nutrients contained within the arterial blood.

However, as with the catheter 10, in order to provide an effective retroperfusion therapy, it is necessary for the at least on expandable balloons 630, 632 to inflate and deflate in an integral fashion to ensure that the venous system is not overloaded and the normal antegrade flow of blood can resume periodically to drain the blood from the vein. Now referring to FIG. 11, at least one embodiment of an autoretroperfusion system 700 is shown. The autoretroperfusion system 700 comprises the catheter 610, a flow unit 710, the source of arterial blood flow 250 previously described in connection with the autoretroperfusion systems 200, 300, the remote module 270 previously described in connection with the autoretroperfusion systems 200, 300, and the fluid source 280 previously described in connection with the autoretroperfusion systems 200, 300. In addition, the retroperfusion system 700 may optionally comprise the connection assembly 310 as described in connection with the retroperfusion system 300. As the flow unit 710 is the only component of the retroperfusion system 700 that has not been previously described in detail herein, the remainder of the description of the system 700 will focus on that component.

Like the flow unit 210 of the autoretroperfusion systems 200, 300, the flow unit 710 is responsible, at least in part, for regulation of the pressure of the arterial blood flow prior to its introduction into the catheter 610 and ultimately the venous system of the brain. In this manner, the retroperfusion system 700 can ensure that when the arterial blood flow is first introduced to the vein, the pressure of the re-routed arterial blood flow has already been reduced such that the thinner venous vessels are protected and the blood pressure is maintain within an acceptable pressure range.

Similar to the flow unit 210 of the autoretroperfusion systems 200, 300, the flow unit 710 of the autoretroperfusion system 700 comprises a proximal end 712, a distal end 714, a body 716 extending between the proximal and distal ends 712, 714, a chamber 720, and an interior 718 extending through the chamber 720 and between the proximal and distal ends 712, 714 of the flow unit 710. Each of the aforementioned components of the flow unit 710 is comprised identically to the related components of the flow unit 210. Accordingly, the distal end 714 of the flow unit 710 further comprises at least one sensor 724 disposed therein, which may or may not be a wired device having a wire component that travels through a sensory port 725 to the remote module 270 (not shown). In addition, the chamber 720 comprises an interior 732 that is in fluid communication with the fluid source 280 (not shown) through at least one port 730.

The flow unit 710 is capable of controlling the pressure and flow rate of the arterial blood traveling through the interior 718 of the flow unit 710 in the same manner as the flow unit 210. Accordingly, the remote module 270 (not shown) can manipulate the volume of the fluid injected and withdrawn from the interior 732 of the chamber 720, thereby altering the diameter of the underlying portion of the interior 718 of the flow unit 710. Thus, as with the chamber 220 of the flow unit 210, the chamber 720 of the flow unit 710 is capable of forming a stenosis within the interior 718 of the flow unit 710 such that the flow of arterial blood therethrough is inhibited, and subsequently removing the stenosis (when a sufficient amount of fluid is withdrawn from the interior 732 of the chamber 720) such that the body 716 and interior 718 of the flow unit 710 are maintained at their standard diameters.

In addition to the aforementioned, the flow unit 710 of the retroperfusion system 700 is further capable of inflating and deflating the at least one balloons 630, 632 of the catheter 610. Specifically, in at least one embodiment of the flow unit 710, the first and/or second balloon ports 634, 635 are in fluid communication with the interior 732 of the chamber 720 such that any fluid injected or withdrawn therefrom necessarily affects the expansion and/or deflation of the at least one balloon 630, 632. As such, the flow unit 710 further comprises at least one conduit in fluid communication with the interior 732 of the chamber 720 configured to couple with the at least one balloon port 634, 365 of the catheter 610 such that the at least one conduit of the flow unit 710 and the at least one balloon port 634, 635 of the catheter 610 are securely coupled and in fluid communication.

Where the catheter 610 comprises a first balloon 630 and a second balloon 632, at least one conduit of the flow unit 710 may be configured such that the balloons 630, 632 can expand in unison and/or independently. For example and without limitation, where the conduits in fluid communication with each of the first and second balloons 630, 632 are fluidly coupled with the interior 732 of the chamber 720, but do not independently interact with the remote module 270 (not shown) nor the fluid source 280 (not shown), the first and second balloons 630, 632 necessarily expand and deflate in substantial unison (taking into account the varying distances the fluid injected into the interior 732 of the chamber 620 must flow through the balloon ports 634, 635 prior to reaching the interiors of the first and second balloons 630, 632).

Figure 11:
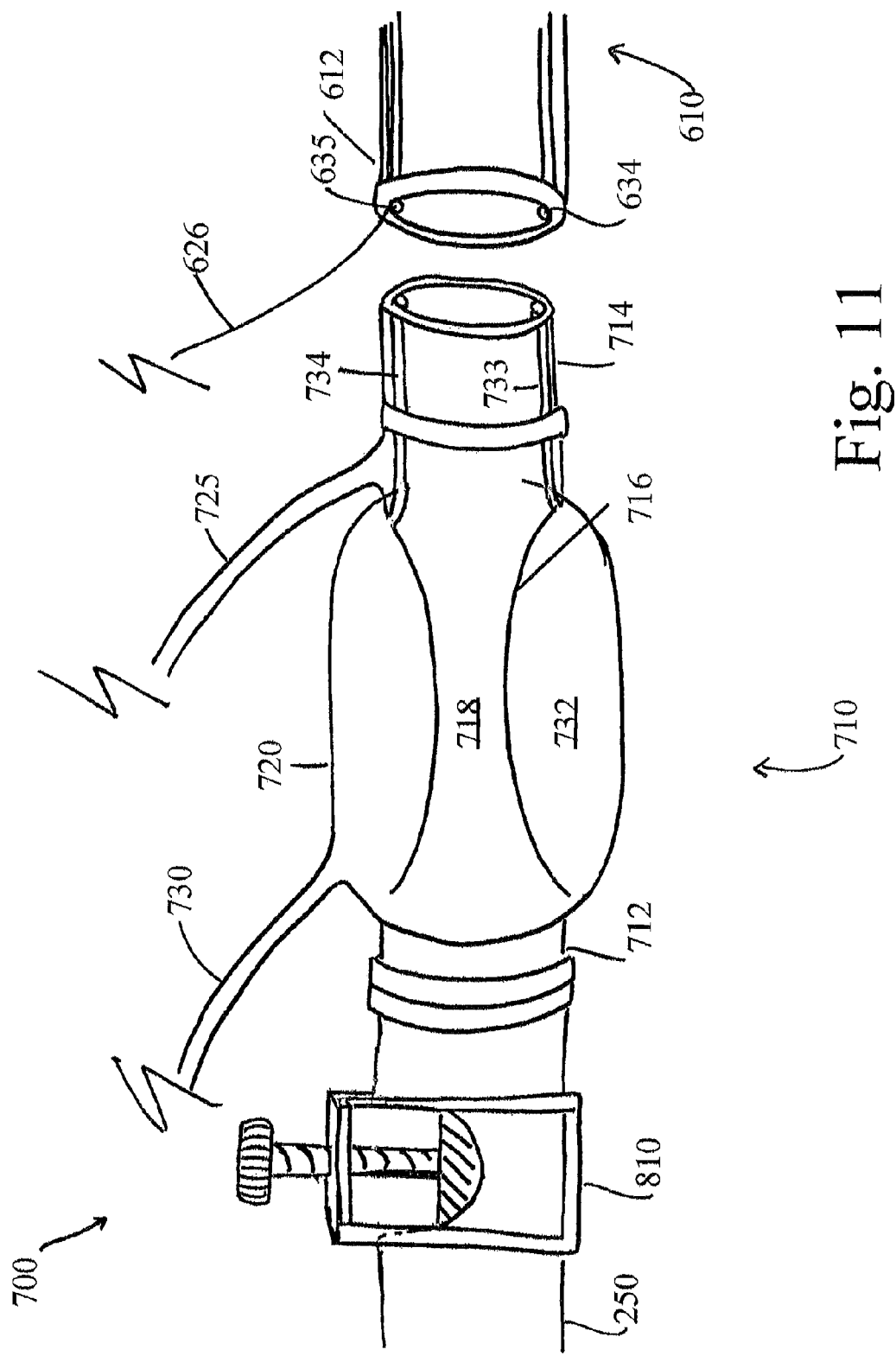
FIG. 11 shows a side view of a retroperfusion system for providing a retroperfusion therapy to an ischemic area of a brain.

As shown in FIG. 11, at least one embodiment of the flow unit 710 comprises a first conduit 733 and a second conduit 734, both of which are in fluid communication with the interior 732 of the chamber 720. Furthermore, each of the conduits 733, 734 extends distally from the chamber 720, along the interior walls of the body 716 and into the distal end 714 of the flow unit 710. In this manner, the first and second conduits 733, 734 may be aligned with the first and second balloon ports 634, 635, respectively such that a secure connection is formed therebetween when the proximal end 612 of the catheter 610 is coupled with the distal end 714 of the flow unit 710.

In addition to being capable of automatically operating the chamber 720 to ensure specific parameters related to the arterial blood flow are met, the remote module 270 may additionally be programmed to actively regulate the expansion and deflation of the at least one balloon 630, 632 of the catheter 610. For example and without limitation, when the first and second balloons 630, 632 are each in independent communication with the fluid source 280 (not shown) and/or the remote module 270 (not shown), the remote module 270 can independently control the expansion and deflation of the first and second balloons 630, 632 in order to achieve optimal performance of the catheter 610. It will be understood that the remote module 270 operates to expand and deflate the chamber 720 of the flow unit 710 (and thus the balloons 630, 632 that, in this at least one embodiment, are in fluid communication therewith) in an identical manner as described with respect to the flow unit 210, the remote module 270.

Furthermore, in at least one non-limiting example, based on the data continuously received from the sensors 624, 724 of the catheter 610 and the flow unit 710, the remote module 270 can automatically adjust the volume of fluid injected into the interior 732 of the chamber 720 (and thus the interiors of the at least one balloon 630, 632 of the catheter 610) in order to expand the balloon(s) 630, 632 to a desired size. Accordingly, the expansion of the at least one balloon 630, 632 occludes the vein in which the catheter 610 is inserted, thereby building the pressure in the venous system, facilitating the perfusion of arterial blood into the capillaries that branch from the vein, and providing support to the catheter 610 to prevent against the catheter 610 from becoming dislodged. Furthermore, the remote module 270 is also capable of automatically adjusting the volume of the fluid withdrawn from the interior 732 of the chamber 720 (and thus the interiors of the at least one balloon 630, 632 of the catheter 610) in order to deflate the balloon(s) 630, 632. This, in turn, allows for the normal antegrade flow of blood to drain from the vein and automatically decreases the pressure in the venous system. Accordingly, by driving the periodic expansion and deflation of the at least one balloon 630, 632 of the catheter 610, the remote module 270 can further manipulate the pressure and flow rates within the autoretroperfusion system 700 and prevent the vein from becoming overloaded.

In at least one embodiment of the autoretroperfusion system 700, the remote module 270 can be driven be an algorithm such that the remote module 270 is capable of executing the inflation and deflation of the chamber 720 of the flow unit 710, as well as the expansion and deflation of the at least one balloon 630, 632 of the catheter 610, pursuant to a set of desired flow parameters, pressure and perfusion rates. In other words, in this at least one embodiment, the remote module 270 automatically manipulates the injection of fluid into and the withdrawal of fluid from the interior 732 of the chamber 720 on an interval basis in order to achieve the arterial blood flow, pressure and any other criterion of interest within the optimal ranges.

In at least one additional embodiment of the retroperfusion system 700, system 700 may further comprise a fixed stenosis. Specifically, the retroperfusion system 700 may further comprise a stenosis component 810 for placement in connection with the source of arterial blood flow 250 in such a manner so as to affect the flow of arterial blood therethrough. Accordingly, the stenosis component 810 can statically manipulate the pressure and/or flow rate of the arterial blood even prior to its introduction into the proximal end 712 of the flow unit 710.

It will be understood that the stenosis component 810 may comprise any fixed stenosis device known in the art provided the stenosis component 810 does not degrade over time, contaminate the system, and/or cause coagulation of the arterial blood. As illustrated in FIG. 11, in at least one embodiment the stenosis component 810 comprises a device designed to be coupled with the exterior wall of the source for arterial blood flow 250 that is capable of applying external compression thereto in order to facilitate the control of the flow rate and pressure of the blood moving through the source of arterial blood flow 250. Specifically, the stenosis component 810 of FIG. 11 comprises a clamp-like device applied to the exterior wall of the source for arterial blood flow 250 in such a manner so as to reduce the diameter of the same.

Despite the at least one example provided in FIG. 11, it will be understood that the stenosis component 810 may comprise any means for providing a fixed stenosis such that a pressure drop is achieved in the blood flowing through the source of arterial blood flow 250. For example and without limitation, in at least one additional embodiment, the stenosis component 810 may comprise a coil or internal balloon designed to be positioned within the source of arterial blood flow 250 and to partially occlude the flow of arterial blood therethrough.

In at least one alternative embodiment of the retroperfusion system 700 comprising the stenosis component 810, the flow unit 710 is configured in such a manner that it does not allow for the manipulation of the diameters of the body 716 and/or interior 718 of the flow unit 710. Accordingly, even though fluid may be injected into or withdrawn from the interior 732 of the chamber 720 as described previously described herein, the diameters of the body 716 and interior 718 of the flow unit 710 are fixed. Thus, in this at least one embodiment, the remote module 270 is solely capable of expanding and deflating the at least one balloon 630, 632 of the catheter 610 through injection and/or withdrawal of a fluid into the interior 732 of the chamber 720 and all other regulation of the arterial blood flow rate and/or pressure is achieved using the stenosis component 810 and/or the fixed diameter of the interior 718 of the flow unit 710.

Figure 12:
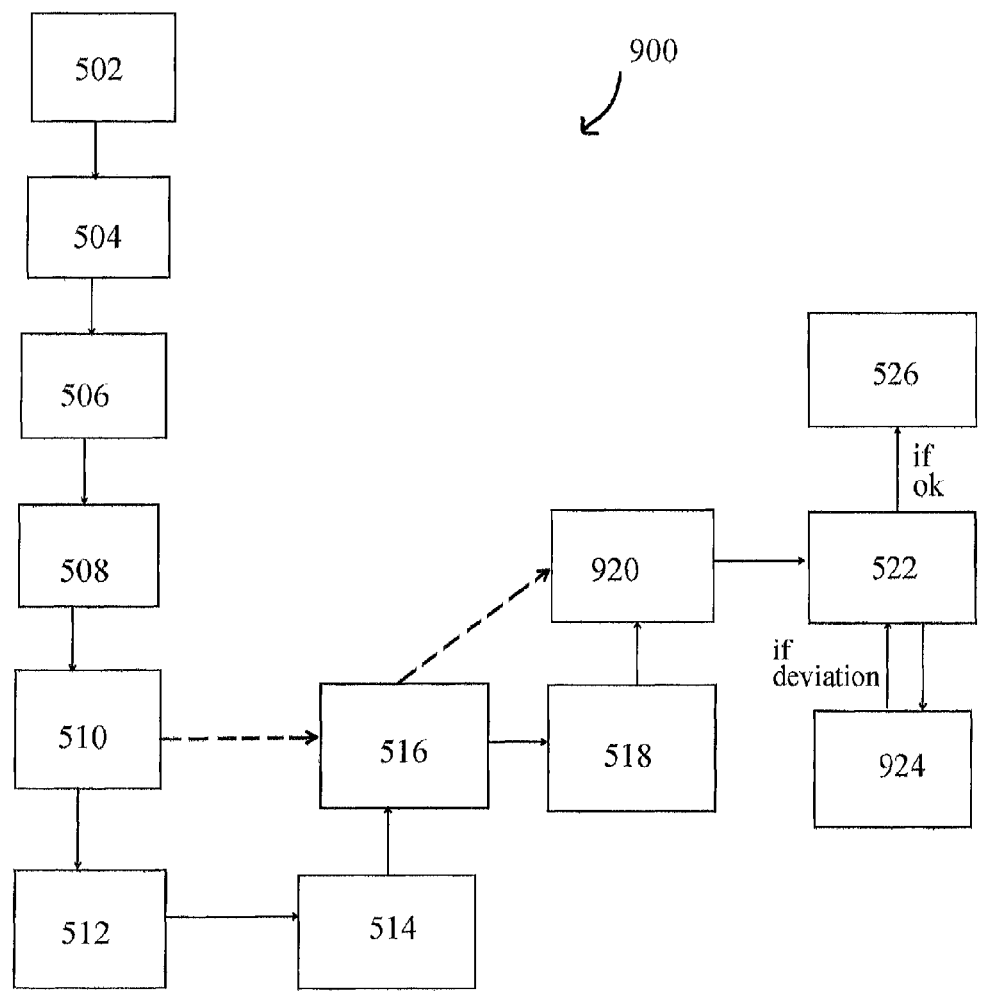
FIG. 12 shows a flow chart of a method for percutaneously delivering the retroperfusion system of FIG. 11 to a targeted cerebral vein in order to provide retroperfusion therapy thereto.

Now referring to FIG. 12, a flow chart of a method 900 for providing retroperfusion therapy to a brain is shown. For ease of understanding, the steps of the method 900 described herein will be discussed relative to the components of the retroperfusion system 700, but it will be appreciated by one skilled in the art that any similar devices and/or systems can be used to perform this method 900. In addition, while the retroperfusion system 700 and the method 900 are described in connection with treating an ischemic area of a brain through catheterization of a venous vessel extending into a penumbral area of a brain, it will be understood that the retroperfusion system 700 and the method 900 described herein may be applied to perform autoretroperfusion on any organ or tissue in need of retroperfusion treatment. Furthermore, it will be understood that the steps of the method 900 referred to using the reference numerals associated with the steps previously described in connection with the method 500 herein are identical to the steps of method 500 having like reference numerals.

In at least one approach to the method 900, at step 502 a topographic image of the ischemic area of the brain 400, including the core ischemic infarct and the ischemic penumbra, is created using conventional imaging techniques. In this manner, a clinician can determine the location of the ischemic infarct and the penumbra. At step 504, an artery of interest (not shown) is percutaneously punctured under local anesthesia with a conventional artery access device or as otherwise known in the art. For example and without limitation, in at least one embodiment, an 18 gauge needle is inserted into the desired artery and the source of arterial blood flow 250 having the stenosis component 810 coupled therewith is positioned within the artery such that a portion of arterial blood is re-routed therethrough, driven by the pulsatile rhythm of the beating heart.

At step 506, a vein of interest is percutaneously punctured under local anesthesia with a conventional venous access device or as otherwise known in the art. For example and without limitation, in at least one embodiment, an 18 gauge needle is inserted into the jugular vein. It will also be appreciated that any other vein may be utilized, provided the vein facilitates retroperfusion of the arterial blood to the desired area of the body. After the vein has been punctured, at step 508, a soft guidewire 40 is inserted into the opening in the vein and advanced into the penumbra region of the brain. This may be facilitated through use of the brain topographic imaging taken at step 502 and/or through x-ray (i.e. fluoroscopy) or other suitable visualization techniques.

After the distal end of the guidewire 40 is positioned in the desired location within the penumbra of the brain, the distal end 614 of the catheter 610 is inserted into the vein following the guidewire 40 at step 510. Specifically, the distal end 614 of the catheter 610 is threaded over the guidewire 40, inserted into the vein and advanced along the main venous system to the target area within the penumbra. Step 510 may be performed under fluoroscopic control or with the aid of other visualization techniques known in the art. Thereafter, the guidewire 40 may optionally be withdrawn from the body through the lumen 18 of the catheter 10 at step 512.

At step 514, the connection assembly 310 may optionally be coupled with the proximal end 612 of the catheter 10 and the distal end 714 of the flow unit 710. The connection assembly 310 is fitted over the distal end 714 of the flow unit 710 and the proximal end 612 of the catheter 610 and forms a leak-free attachment with both components 610, 710. Furthermore, in the at least one embodiment of the method 900 where the at least one guidewire 40 was not withdrawn from the patient's body at step 512, the proximal end of the at least one guidewire 40 is threaded through the distal end 314 and the limb component 318 of the connection assembly 310 such that the at least one guidewire 40 extends through the interior 322 of the limb component 318.

At step 516, the flow unit 710 is coupled with the source of arterial blood flow 250 and begins to receive arterial blood from the punctured artery within the interior 718 thereof. In this manner, the arterial blood re-routed from the artery of interest (not shown) by the source of arterial blood flow 250 is allowed to flow through the source of arterial blood flow 250 and into the proximal end 712 of the flow unit 710 in a pulsatile fashion pursuant to the rhythm of the patient's heartbeat. In addition, due to the inclusion of the stenosis component 810 on or in the source of the arterial blood flow, the flow rate and/or pressure (depending on the configuration of the particular stenosis component 810) is adjusted as the arterial blood flows past the location of the source of arterial blood flow 250 where the stenosis component 810 is coupled therewith.

At step 514, the proximal end 612 of the catheter 610 and the distal end 714 of the flow unit 710 are securely coupled together. In the at least one embodiment of the retroperfusion system 700 that further comprises the connection assembly 310, at step 518 the connection assembly 310 initiates the injection of gas into the interiors 320, 322 of the body 316 and the limb component 318 such that the proximal end 612 of the catheter 610 and the distal end 714 of the flow unit 710 may be secured together under sterile conditions. In addition, at step 518, if the at least one guidewire 40 has not previously been withdrawn from the patient's body through the lumen 618 of the catheter 610 at step 512, the at least one guidewire 40 is now removed from the patient through the limb component 318 of the connection assembly 310.

At step 920, the distal end 214 of the flow unit 210 and the proximal end 12 of the catheter 10 are securely coupled with one another and the arterial blood from the artery of interest is pumped in synchrony with the patient's sinus rhythm through the source of arterial blood flow 250, past the stenosis component 810, and into the flow unit 710. In the at least one embodiment of the retroperfusion system 700 where the diameter of the interior 718 of the flow unit 710 is dynamically regulated by the remote module 270, the pressure and flow of the arterial blood is further regulated by the remote module 270 through use of the chamber 720. Thereafter, the arterial blood having pressure and flow values falling within the appropriate ranges flows into the lumen 618 of the catheter 610 where the arterial blood is perfused in a retrograde fashion into the vein at a target location within the penumbra region of the brain. Accordingly, in at least one embodiment, step 920 further comprises the initial manipulation of the diameter of the interior 718 of the flow unit 710 and the initial expansion and deflation of the at least one expandable balloon 630, 632 of the catheter 610 as controlled by the remote module 270. However, it will be understood that, in the at least one embodiment of the retroperfusion system 700 wherein the interior 718 of the flow unit 710 is fixed, step 920 does not include manipulation of the interior 718 diameter and, as such, the remote module 270 only facilitates the initial expansion and deflation of the at least one expandable balloon 630, 632 of the catheter 610.

At step 522, the remote module 270 assesses whether or not the data measured by the at least one sensors 624, 724 of the catheter 610 and the flow unit 710 fall within the acceptable, pre-programmed ranges. In the event the remote module 270 detects any deviation in the data falling outside of the pre-defined allowable ranges, the method 900 proceeds to step 924. At step 924, the remote module 270 makes adjustments to the autoretroperfusion system 700 until the data received from the sensors 624, 724 indicates that the deviation has been corrected and the data falls within the acceptable parameters. For example, in the at least one embodiment of the retroperfusion system 700 wherein the interior 718 of the flow unit 710 is fixed, the remote module 270 may adjust the rate at which the at least one balloon 630, 632 of the catheter 610 is expanded and deflated in order to manipulate the flow and/or pressure values of the arterial blood perfusing through the catheter 610 and into the vein. Alternatively, where the diameter of the interior 718 of the flow unit 710 is adjustable, the remote module 270 may adjust the rate of injection and/or withdrawal of fluid from the chamber 220 and/or the volume of fluid injected or withdrawn from the interior 232 of the chamber 220 in order to affect the expansion and deflation of the balloons 630, 632 and/or the diameter of the interior 718 (and thus degree of stenosis) of the flow unit 710. Accordingly, at step 924, the remote module 270 automatically adjusts the flow and/or pressure of the arterial blood flowing through the flow unit 710 pursuant to the continuous stream of data received from the at least one sensor 624 of the catheter 610 and the at least one sensor 724 of the flow unit 710.

When, either at step 522 or step 924, the remote module 270 verifies that all of the data parameters are in order, the method 900 advances to step 526. At step 526, the remote module 270 defines an arterial blood pressure and flow time cycle based on the data the remote module 270 continuously receives from the at least one sensor 624 of the distal end 614 of the catheter 610 and the at least one sensor 724 of the distal end 714 of the flow unit 710. After the remote module 270 has defined the pressure and flow time cycle, the remote module 270 establishes the same through the interval operation of the fluid source 280 and inflation and/or deflation of the balloons 630, 632 and/or, if applicable, the adjustment of the diameter of the interior 718 of the flow unit 710. In this manner, the autoretroperfusion system 700 delivers continuous autoretroperfusion therapy to the penumbra of the brain such that the cells within the penumbra can be maintained for an extended period of time following an acute stroke event.

The devices, systems and methods described herein provide numerous benefits over the devices, systems and methods of the prior art. The systems 200, 300, 700 allow for a bridge retroperfusion therapy to be safely delivered to stroke patients such that other treatment therapies that were previously not available may be applied. Furthermore, the devices, systems and methods described herein are minimally invasive, completely reversible, and decrease the risk of complications seen with conventional treatments.

While the devices, systems and methods described herein are presented with respect to specific anatomy and treatment examples, as one of ordinary skill in the art would recognize, the systems 200, 300 and 700, the components thereof, and the methods 500, 900 may be expanded to any organ, limb or body structure that would benefit from a safe and controllable retroperfusion therapy.

While various embodiments of devices and systems for auto-retroperfusion of the cerebral venous system and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A catheter for controlling blood perfusion pressure, the catheter comprising:
   a body having a proximal open end, a distal end, a lumen extending between the proximal open end and the distal end, and a plurality of orifices disposed thereon, each of the orifices in fluid communication with the lumen;
   at least one expandable balloon, each of the at least one expandable balloons coupled with the body, having an interior that is in fluid communication with the lumen and adapted to move between an expanded configuration and a deflated configuration; and
   at least one sensor coupled with the distal end of the body, each of the at least one sensors in communication with a remote device and adapted to gather data relating to a fluid flowing through the lumen;
   wherein the catheter is configured to be coupled to a flow unit for regulating the flow and pressure of a fluid and the remote device is configured to automatically adjust the flow unit to effect either or both of the flow and pressure of the fluid based on the data gathered by the at least one sensor.

2. The catheter of claim 1, wherein one or more of the at least one sensors is adapted to transmit the gathered data to the remote device.

3. The catheter of claim 1, wherein the body is configured for placement within a venous vessel.

4. The catheter of claim 1, wherein the body further comprises one or more pores disposed thereon to facilitate fluid communication between the lumen and the interior of each of the at least one expandable balloons.

5. The catheter of claim 4, wherein each of the at least one expandable balloons is adapted to move from the deflated configuration to the expanded configuration when a fluid flows through the lumen of the body, through the one or more pores, and into the interior of the expandable balloon.

6. The catheter of claim 1, further comprising:
   a sheath having a proximal end, a distal end, and an interior, the interior configured to slidably receive the body of the catheter therein.

7. The catheter of claim 2, wherein at least one of the at least one sensors is coupled with a sensor cable, the sensor cable disposed within the interior of the lumen such that the sensor cable extends through the proximal end of the body and adapted to transmit the gathered data to the remote device.

8. The catheter of claim 1, wherein the lumen of the body is configured to slidably receive at least one guidewire therethrough, and the distal end of the body is configured to allow the at least one guidewire to extend therethrough.

9. A flow unit for regulating the flow and pressure of a fluid, the flow unit comprising:
   an elongated body having an open proximal end, an open distal end, an interior extending between the open proximal end and the open distal end, and a chamber surrounding at least a portion of the elongated body, the chamber adapted to expand and deflate and comprising an interior and at least one port in fluid communication with the interior of the chamber and adapted to couple with a fluid source;
   at least one sensor disposed at or near the distal end of the elongated body, each of the at least one sensors in communication with a remote device and adapted to gather data relating to a fluid flowing through the interior of the elongated body;
   wherein the flow unit is configured to be coupled to a catheter for controlling blood perfusion pressure and the remote device is configured to automatically expand or deflate the chamber of the elongated body based on the data gathered by the at least one sensor.

10. The flow unit of claim 9, wherein:
    one or more of the at least one sensors is adapted to transmit the gathered data to the remote device; and
    the remote device is configured to ascertain at least one optimal flow parameter for the fluid flowing through the interior of the elongated body based on the gathered data and to automatically manipulate the chamber to satisfy the at least one optimal flow parameter.

11. The flow unit of claim 9, wherein:
    a section of the interior of the elongated body associated with the portion surrounded by the chamber comprises a first diameter when the chamber is deflated and a second diameter when the chamber in expanded, the second diameter being less than the first diameter; and
    the remote device is in fluid communication with at least one balloon, the at least one balloon configured to move between expanded and deflated configurations in conjunction with the expansion or deflation of the chamber of the elongated body as driven by the remote device.

12. The flow unit of claim 9, wherein when the chamber is expanded, the interior of the chamber is adapted to exert a compressive force on the portion of elongated body surrounded thereby.

13. A system for providing a retroperfusion therapy to a venous vessel, the system comprising:
- a catheter for controlling blood perfusion pressure, the catheter comprising:
  - a body having a proximal open end, a distal end, a lumen extending between the proximal open end and the distal end, and a plurality of orifices disposed thereon, each of the orifices in fluid communication with the lumen, and
  - at least one expandable balloon, each of the at least one expandable balloons coupled with the body, having an interior that is in fluid communication with the lumen, and adapted to move between an expanded configuration and a deflated configuration; and
- a flow unit for regulating the flow and pressure of a fluid; and
- a connection assembly for providing a sterile environment, the connection assembly comprising a cover defining an interior configured to encase at least a portion of the flow unit and at least a portion of the body of the catheter therein.

14. The system of claim 13, further comprising:
an arterial blood flow device comprising a proximal end, a distal end configured to couple with the proximal end of the elongated body of the flow unit, and an interior extending between the proximal end and the distal end, the proximal end, the distal end and the interior each configured to allow arterial blood to flow therethrough.

15. The system of claim 13, wherein the flow unit comprises:
- an elongated body having an open proximal end, an open distal end coupled with the open proximal end of the body of the catheter, an interior extending between the open proximal end and the open distal end of the elongated body, and a chamber surrounding at least a portion of the elongated body, the chamber adapted to expand and deflate and comprising an interior and at least one port in fluid communication with the interior of the chamber and adapted to couple with a fluid source, and
- at least one sensor disposed at or near the distal end of the elongated body, each of the at least one sensors adapted to gather data from a fluid flowing through the interior of the elongated body.

16. The system of claim 15, wherein at least one of the at least one sensors of the flow unit is adapted to transmit the gathered data to a remote device.

17. The system of claim 15, in which at least one of the at least one sensors comprises a sensor comprising a wire coupled with the remote device and the elongated body of the flow unit further comprises a sensory port adapted to house the wire of the at least one sensor.

18. The system of claim 13, wherein:
the cover of the connection assembly further comprises a body portion and a limb component extending from the body portion, and the interior of the connection assembly extends between the body portion and the limb component and is configured to encase the distal end of the elongated body of the flow unit and the proximal end of the body of the catheter therein; and
the connection assembly further comprises:
- at least one flushing port in fluid communication with a gas supply and the interior of the cover; and
- at least one valve in fluid communication with the interior of the cover, the at least one valve adapted to drain gas from within the interior of the cover.

19. The system of claim 13, wherein the catheter further comprises at least one sensor coupled with the distal end of the body, each of the at least one sensors adapted to gather data on a fluid flowing through the lumen of the catheter and transmit the gathered data to a remote device.

20. The system of claim 15, wherein the chamber of the flow unit is adapted to compress the portion of the elongated body surrounded thereby when the chamber is expanded such that a stenosis is formed within a section of the interior of the elongated body associated with the portion surrounded by the chamber.

* * * * *